(12) United States Patent
Eidinger et al.

(10) Patent No.: US 10,571,423 B2
(45) Date of Patent: Feb. 25, 2020

(54) SYSTEMS AND METHODS FOR LOCATING A STUD

(71) Applicant: STANLEY BLACK & DECKER INC., New Britain, CT (US)

(72) Inventors: Bruce Eidinger, Meriden, CT (US); Yong Cushing, Beacon Falls, CT (US); Michael Murray, Baltimore, MD (US); Bianca Linay, Hartford, CT (US)

(73) Assignee: STANLEY BLACK & DECKER INC., New Britain, CT (US)

( * ) Notice: Subject to any disclaimer, the term of this patent is extended or adjusted under 35 U.S.C. 154(b) by 247 days.

(21) Appl. No.: 15/632,175

(22) Filed: Jun. 23, 2017

(65) Prior Publication Data
US 2017/0370868 A1    Dec. 28, 2017

Related U.S. Application Data

(60) Provisional application No. 62/354,176, filed on Jun. 24, 2016.

(51) Int. Cl.
*G01N 27/24* (2006.01)
*G01V 3/15* (2006.01)
(Continued)

(52) U.S. Cl.
CPC ............ *G01N 27/24* (2013.01); *G01V 3/02* (2013.01); *G01V 3/088* (2013.01); *G01V 3/15* (2013.01)

(58) Field of Classification Search
CPC . G01N 27/24; G01V 3/02; G01V 3/15; G01V 3/88
See application file for complete search history.

(56) References Cited

U.S. PATENT DOCUMENTS 3,480,857 A    11/1969    Bialko et al.
3,588,640 A    6/1971    Fabricius
(Continued)

FOREIGN PATENT DOCUMENTS

CN    106841819 A    6/2017
DE    8615489    7/1987
(Continued)

OTHER PUBLICATIONS

International Preliminary Report on Patentability issued for corresponding International Patent Application No. PCT/US2017/039126, dated Oct. 16, 2018.
(Continued)

*Primary Examiner* — Dominic E Hawkins
(74) *Attorney, Agent, or Firm* — Pillsbury Winthrop Shaw Pittman LLP

(57) ABSTRACT

This disclosure describes a stud sensor configured to locate a stud. The stud sensor includes a housing and a sensor carried by the housing. The sensor includes two or more electrodes. The two or more electrodes are configured to form a substantially circular configuration. The stud sensor further comprises one or more processors carried by the housing. The one or more processors are communicatively coupled with the sensor. The one or more processors are configured by machine-readable instructions to calculate a stud location by measuring a change in capacitance from a fixed capacitance of a wall structure as the stud sensor is moved along a surface of the wall structure; and generate one or more signals to report a result relating to a location of a stud.

20 Claims, 20 Drawing Sheets

(51) Int. Cl.
*G01V 3/08* (2006.01)
*G01V 3/02* (2006.01)

(56) References Cited

U.S. PATENT DOCUMENTS

| | | | |
|---|---|---|---|
| 4,016,490 A | 4/1977 | Weckenmann et al. | |
| 4,045,728 A | 8/1977 | Fletcher et al. | |
| 4,158,216 A | 6/1979 | Bigelow | |
| 4,264,903 A | 4/1981 | Bigelow | |
| 4,464,622 A | 8/1984 | Franklin | |
| 4,636,714 A | 1/1987 | Allen | |
| 4,766,368 A | 8/1988 | Cox | |
| 4,853,617 A | 8/1989 | Douglas et al. | |
| 4,992,741 A | 2/1991 | Douglas et al. | |
| 5,148,108 A | 9/1992 | Dufour | |
| D339,074 S | 9/1993 | Dufour | |
| 5,508,662 A | 4/1996 | Guichard et al. | |
| 5,812,057 A | 9/1998 | Hepworth et al. | |
| 5,863,445 A | 1/1999 | Geisel et al. | |
| 5,917,314 A | 6/1999 | Heger et al. | |
| 6,023,159 A | 2/2000 | Heger | |
| 6,211,662 B1 | 4/2001 | Bijawat et al. | |
| 6,215,293 B1 | 4/2001 | Yim | |
| 6,348,862 B1* | 2/2002 | McDonnell | B60N 2/002 180/272 |
| 6,466,036 B1 | 10/2002 | Philipp | |
| 6,650,111 B2 | 11/2003 | Christensen | |
| 6,653,826 B2 | 11/2003 | Beha | |
| 6,894,508 B2 | 5/2005 | Sanoner et al. | |
| 6,914,930 B2 | 7/2005 | Raskin et al. | |
| 6,922,063 B2* | 7/2005 | Heger | G01C 9/14 324/658 |
| 6,939,299 B1 | 9/2005 | Petersen et al. | |
| 7,027,480 B2 | 4/2006 | Marshall et al. | |
| 7,031,367 B2 | 4/2006 | Marshall et al. | |
| 7,059,057 B2 | 6/2006 | Raskin et al. | |
| 7,134,212 B2 | 11/2006 | Marshall et al. | |
| 7,193,405 B2 | 3/2007 | Murray | |
| 7,288,946 B2 | 10/2007 | Hargreaves et al. | |
| 7,301,350 B2 | 11/2007 | Hargreaves et al. | |
| 7,391,217 B2 | 6/2008 | Linse et al. | |
| 7,423,437 B2 | 9/2008 | Hargreaves et al. | |
| 7,453,270 B2 | 11/2008 | Hargreaves et al. | |
| 7,516,544 B1 | 4/2009 | Petunin | |
| 7,521,941 B2 | 4/2009 | Ely et al. | |
| 7,583,092 B2 | 9/2009 | Reynolds et al. | |
| 7,677,107 B2 | 3/2010 | Nunez et al. | |
| 7,683,641 B2 | 3/2010 | Hargreaves et al. | |
| 7,750,649 B2 | 7/2010 | Ely et al. | |
| 7,759,939 B2 | 7/2010 | Skultety-Betz et al. | |
| 7,804,307 B1 | 9/2010 | Bokma | |
| 7,816,920 B2 | 10/2010 | Qin et al. | |
| 7,863,909 B2 | 1/2011 | Keith | |
| 7,880,479 B2 | 2/2011 | Liao et al. | |
| 7,882,478 B2 | 2/2011 | Petunin | |
| 7,924,103 B2 | 4/2011 | Kuehn | |
| 7,940,048 B2 | 5/2011 | Skultety-Betz | |
| 7,948,245 B2 | 5/2011 | Hargreaves et al. | |
| 7,986,153 B2 | 7/2011 | Easter | |
| 7,997,544 B2 | 8/2011 | Fong | |
| 8,026,711 B2 | 9/2011 | Krapf et al. | |
| 8,237,456 B2 | 8/2012 | Dubery | |
| 8,251,157 B2 | 8/2012 | Gray et al. | |
| 8,258,777 B2 | 9/2012 | Chen | |
| 8,269,479 B2 | 9/2012 | Krapf et al. | |
| 8,358,226 B2* | 1/2013 | Reynolds | G06F 3/0202 178/18.06 |
| 8,400,209 B2 | 3/2013 | Ujvari | |
| 8,476,912 B2 | 7/2013 | Dorrough | |
| 8,487,638 B2 | 7/2013 | Osaki et al. | |
| 8,487,788 B2 | 7/2013 | Reynolds et al. | |
| 8,593,163 B2 | 11/2013 | Dorrough | |
| 8,669,772 B2 | 3/2014 | Dorrough | |
| 8,736,000 B1 | 5/2014 | Manginell et al. | |
| 8,736,283 B2 | 5/2014 | Dorrough | |
| 8,791,708 B2 | 7/2014 | Dorrough | |
| 8,836,347 B2 | 9/2014 | Dorrough | |
| 8,836,350 B2 | 9/2014 | Peter | |
| 8,884,633 B2 | 11/2014 | Dorrough | |
| 8,981,781 B2 | 3/2015 | Haldner et al. | |
| 9,035,662 B2 | 5/2015 | Reime | |
| 9,110,551 B2 | 8/2015 | Lesonen | |
| 9,176,636 B1 | 11/2015 | Maharyta et al. | |
| 9,194,688 B2 | 11/2015 | Thoss et al. | |
| 9,194,950 B2 | 11/2015 | Watts et al. | |
| 9,228,969 B2 | 1/2016 | Dorrough | |
| 9,304,223 B2* | 4/2016 | DeMaira | G01V 3/08 |
| 9,398,224 B2 | 7/2016 | Haldner et al. | |
| 9,404,727 B2 | 8/2016 | Baldwin et al. | |
| 9,500,686 B1 | 11/2016 | Wilson et al. | |
| 9,531,380 B2 | 12/2016 | Dubery | |
| D782,344 S | 3/2017 | Sullian | |
| 9,638,823 B2 | 5/2017 | Albrecht et al. | |
| 9,658,326 B2 | 5/2017 | Watts et al. | |
| 9,664,808 B2 | 5/2017 | Nguyen et al. | |
| 9,726,518 B2 | 8/2017 | Widmer et al. | |
| 9,810,744 B2 | 11/2017 | Reitsma | |
| 10,133,426 B2 | 11/2018 | Den Boer et al. | |
| 10,203,424 B2* | 2/2019 | Wang | G01R 27/2605 |
| 2001/0007420 A1 | 7/2001 | Bijawat et al. | |
| 2006/0013278 A1 | 1/2006 | Raskin et al. | |
| 2007/0210785 A1 | 9/2007 | Sanoner et al. | |
| 2008/0084212 A1 | 4/2008 | Wieland | |
| 2008/0110038 A1 | 5/2008 | Sergyeyenko | |
| 2008/0186010 A1 | 8/2008 | Skultety-Betz et al. | |
| 2008/0238403 A1* | 10/2008 | Sanoner | G01V 3/088 324/67 |
| 2008/0297175 A1 | 12/2008 | Wu | |
| 2008/0303517 A1 | 12/2008 | Skultety-Betz et al. | |
| 2009/0021248 A1 | 1/2009 | Bernard et al. | |
| 2010/0019768 A1 | 1/2010 | Qin et al. | |
| 2010/0090866 A1 | 4/2010 | Chen et al. | |
| 2011/0095771 A1* | 4/2011 | Reime | G01V 3/088 324/686 |
| 2011/0156724 A1 | 6/2011 | Bokma et al. | |
| 2011/0243476 A1* | 10/2011 | Sieracki | G01V 3/15 382/291 |
| 2014/0009171 A1 | 1/2014 | Ujvari | |
| 2014/0145704 A1 | 5/2014 | Krapf et al. | |
| 2014/0239981 A1* | 8/2014 | Zibold | G01V 3/088 324/680 |
| 2015/0145518 A1 | 5/2015 | Haldner et al. | |
| 2015/0177878 A1 | 6/2015 | Cheng et al. | |
| 2015/0309203 A1 | 10/2015 | Monroe | |
| 2016/0377758 A1* | 12/2016 | Dorrough | G01R 27/2605 324/672 |
| 2017/0003799 A1 | 1/2017 | Tateda | |
| 2017/0131426 A1 | 5/2017 | Sgarz et al. | |
| 2017/0153349 A1 | 6/2017 | Krapf et al. | |
| 2017/0153350 A1 | 6/2017 | Krapf et al. | |
| 2017/0153356 A1 | 6/2017 | Zibold | |
| 2017/0248727 A1 | 8/2017 | Nguyen et al. | |
| 2017/0272071 A1 | 9/2017 | Koyuncu et al. | |
| 2017/0328740 A1 | 11/2017 | Widmer et al. | |
| 2018/0279875 A1 | 10/2018 | Moreau et al. | |
| 2018/0303340 A1 | 10/2018 | Moreau et al. | |

FOREIGN PATENT DOCUMENTS

| | | |
|---|---|---|
| DE | 19801827 | 6/1999 |
| DE | 102012223872 | 6/2014 |
| EP | 0 249 110 | 5/1991 |
| EP | 0551606 B1 | 9/1996 |
| EP | 1 194 740 | 10/2002 |
| EP | 1 341 005 | 9/2003 |
| EP | 1 723 444 | 11/2006 |
| EP | 1811530 A2 | 7/2007 |
| EP | 1 975 606 | 10/2008 |
| EP | 2 189 819 | 5/2010 |
| EP | 1 747 483 | 6/2010 |
| EP | 2 388 623 | 11/2012 |
| EP | 2 433 159 | 4/2013 |
| EP | 1278077 B1 | 5/2013 |

(56) References Cited

FOREIGN PATENT DOCUMENTS

| EP | 2565683 B1 | 11/2013 |
|---|---|---|
| EP | 2651036 B1 | 9/2014 |
| EP | 2542921 B2 | 4/2019 |
| GB | 2321787 A | 8/1998 |
| GB | 2404091 A | 1/2005 |
| JP | 2001-315075 A | 11/2001 |
| RU | 2012142889 | 4/2014 |
| WO | WO 2015/157233 | 10/2015 |
| WO | 2017223523 A1 | 12/2017 |

OTHER PUBLICATIONS

Texas Instruments CapTIvate™ peripheral. Technology Guide 1.60,00.00 [online]. Texas Instruments, 2017 [retrieved on Feb. 21, 2018]. Retrieved from the Internet: <URL: software-dl.ti.com/msp430/msp430_public_sw/mcu/msp430/CapTIvate_Design_Center/latest/exports/docs/users_guide/html/CapTIvate_Technology_Guide_html/markdown/ch_technology.html>.

CapTIvate™ Design Center GUI for MSP430™ Capacitive Sensing MCUs [online]. Texas Instruments, 2017 [retrieved on Feb. 21, 2018]. Retrieved from the Internet: <URL: www.ti.com/tool/MSPCAPTDSNCTR>.

International Search Report and Written Opinion issued for corresponding International Patent Application No. PCT/US2017/039126, dated Sep. 21, 2017.

Written Opinion of the International Preliminary Examining Authority (PCT Rule 66) issued for corresponding International Patent Application No. PCT/US2017/039126, dated Jul. 16, 2018.

Texas Instruments document LDC1612, LDC1614 Multi-Channel 28-Bit Inductance to Digital Converter (LDC) for Inductive Sensing, Dec. 2014, revised Mar. 2018.

\* cited by examiner

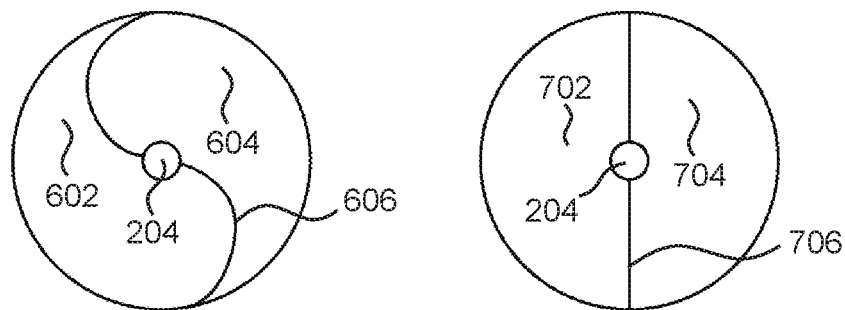
FIG. 5
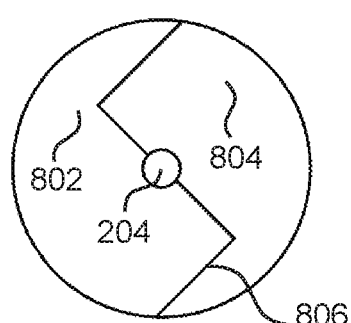
FIG. 6
FIG. 7
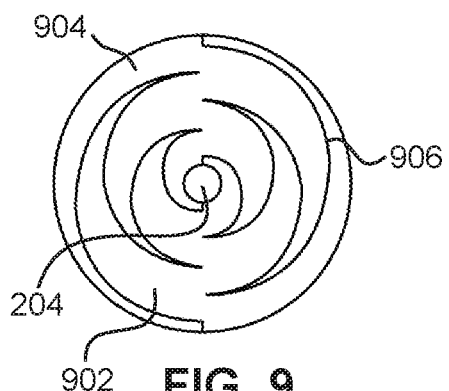
FIG. 8
FIG. 9

| Wall depth (in.) | Minimum square electrode area (sq. in.) |
|---|---|
| 0.5 | 0.095 |
| 0.75 | 0.165 |
| 1.0 | 0.1975 |
| 1.5 or above | 0.4425 |

SYSTEMS AND METHODS FOR LOCATING A STUD

CROSS-REFERENCE TO RELATED APPLICATION

This application claims priority and benefit to U.S. Provisional Application No. 62/354,176, filed on Jun. 24, 2016, and titled "STUD FINDER", the entire content of which is incorporated herein by reference.

BACKGROUND

1. Field

The present disclosure pertains to systems and methods for locating an object, such as a stud, behind the surface of a wall structure or other structure.

2. Description of the Related Art

There are various existing sensing devices for sensing and locating objects behind walls and other building surfaces. One type of sensing device uses capacitive sensors for locating studs behind the surface of the wall or other structure. One aspect of the present application provides an improvement in stud sensors, and in particular capacitive sensors for use in a stud sensing apparatus.

SUMMARY

Accordingly, one or more aspects of the present disclosure relate to a stud sensor configured to locate a stud. The stud sensor comprises a housing and a sensor carried by the housing. The sensor comprises two or more electrodes. The two or more electrodes are configured to form a substantially circular configuration. The stud sensor further comprises one or more processors carried by the housing. The one or more processors are communicatively coupled with the sensor. The one or more processors are configured by machine-readable instructions to calculate a stud location by measuring a change in capacitance from a fixed capacitance of a wall structure as the stud sensor is moved along a surface of the wall structure; and generate one or more signals to report a result relating to a location of a stud.

Another aspect of the present disclosure relates to a stud sensor configured to locate a stud. The stud sensor comprises a housing and a sensor carried by the housing. The sensor comprises two or more interdigitating electrodes. The stud sensor further comprises one or more processors carried by the housing. The one or more processors are communicatively coupled with the sensor. The one or more processors are configured by machine-readable instructions to calculate a stud location by measuring a change in capacitance from a fixed capacitance of a wall structure as the stud sensor is moved along a surface of the wall structure; and generate one or more signals to report a result relating to a location of a stud.

Still another aspect of present disclosure relates to a method for locating a stud with a stud sensor configured to locate a stud. The stud sensor comprises a housing and a sensor carried by the housing. The stud sensor comprises two or more electrodes configured to form a substantially circular configuration. The stud sensor comprises audio and/or visual indicators carried by the housing, and one or more processors communicatively coupled with the two or more electrodes and the audio and/or visual indicators. The one or more processors are configured to generate output signal to the audio and/or visual indicators when a result relating to a location of a stud is determined. A hole is provided through the housing and substantially centered between the sensors. The method comprises calculating a stud location by measuring a change in capacitance from a fixed capacitance of a wall structure as a back surface of the stud sensor housing is moved along a surface of the wall structure; reporting a result relating to a location of a stud based on the change in capacitance; indicating the result relating to the location of the stud via the audio and/or visual indicators; and wherein the hole is aligned with the location of the stud when the audio and/or indicators provide the indication irrespective of the angle at which the wall engaged back surface of the housing is oriented with respect to the wall.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 5 is a wall depth table according to one or more embodiments.

FIG. 6 illustrates two electrodes forming a substantially circular configuration according to one or more embodiments.

FIG. 7 illustrates two electrodes forming a substantially circular configuration according to one or more embodiments.

FIG. 8 illustrates two electrodes forming a substantially circular configuration according to one or more embodiments.

FIG. 9 illustrates two electrodes forming a substantially circular configuration according to one or more embodiments.

DETAILED DESCRIPTION OF EXEMPLARY EMBODIMENTS

Figure 1A:
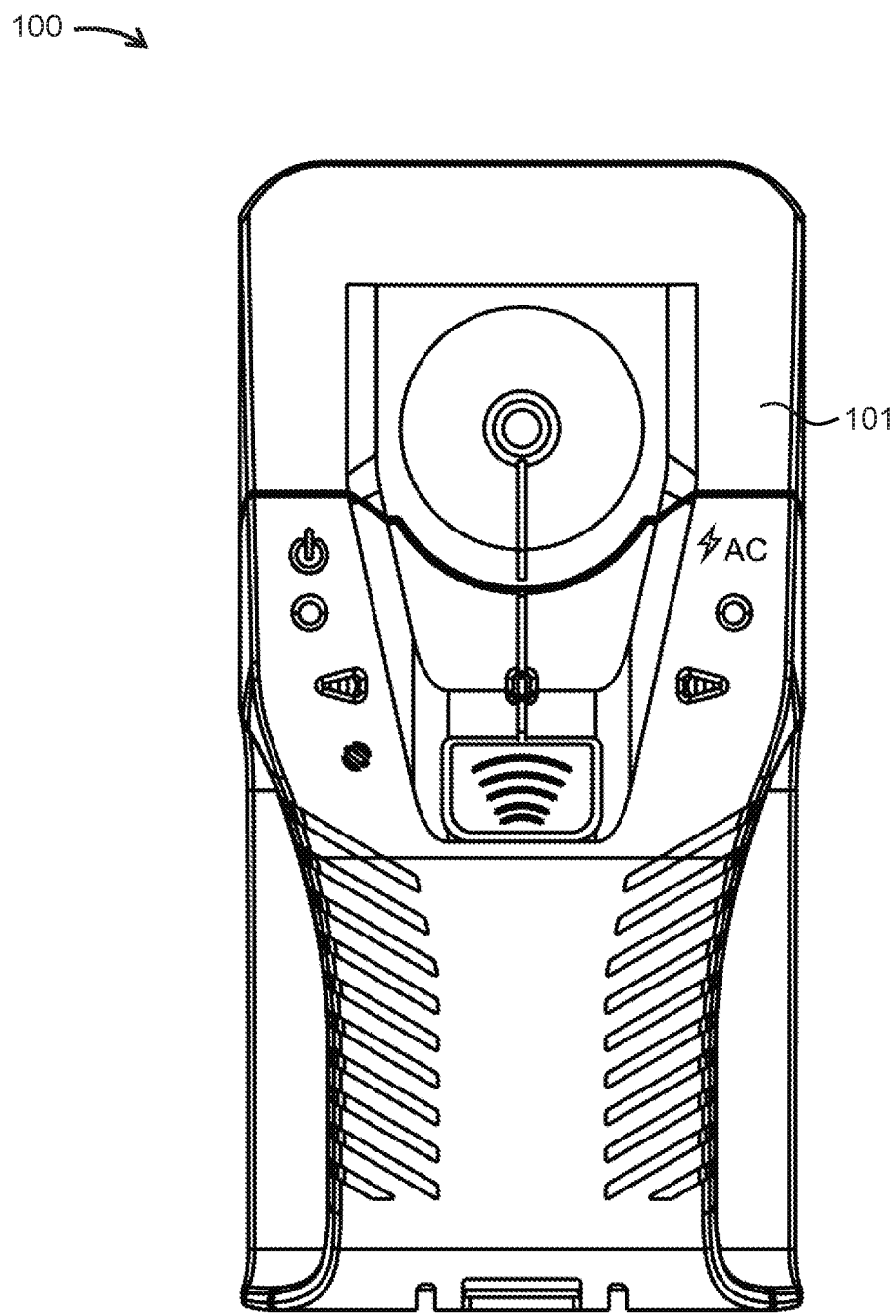
FIG. 1A depicts an exemplary front view of a stud sensing/stud detecting apparatus.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the use of the term "stud" may refer to any hidden object behind the surface of a wall structure, including but not limited to a stud, an alternating current (AC) line, etc. As used herein, the use of the term "wall structure" or "wall" may refer to any surface such as a wall, floor, ceiling, roof, etc. As used herein, the use of the term "substantially circular" is not limited to a circle. Rather, this term refers to circles, ovals, or other rounded shapes. In addition, the term refers to multi-sided shapes approximating a circle. For example, the term refers to octagons or other multi-sided shapes with even more sides than eight. As used herein, the use of the term "square" may refer to square, substantially square, rectangular, or substantially rectangular. As used herein, the use of the term "diamond" may refer to diamond or substantially diamond in shape. As used herein, the use of the term "pyramid" may refer to pyramid or substantially pyramid in shape.

Current stud sensing devices in the market tend to utilize a single square or rectangular shaped electrode (also referred to herein as a stud sensor). Such stud sensing devices may work if a user moves the stud sensor in a linear and horizontal fashion along a surface of a wall structure. However, a human's arm does not always move accurately in a linear line. Rather, a human's arm often moves in an arc like shape, or in another non-linear fashion, especially when the arm is fully stretched out. For example, if a person is reaching far up on a wall structure to try to locate a stud to hang a painting, the person's arm may move in an arc like fashion. Oftentimes people do not maintain the stud sensors in a perfectly vertical orientation, and moreover do not move in a linear and horizontal fashion.

Various embodiments according to the present disclosure utilize electrodes that form substantially circular configurations (as defined herein). The use of a substantially circular configuration for the electrodes provisions a user to approach the stud with the stud sensor at an angle, arc or in a non-linear fashion. A stud locating indicia on the housing will enable the user to identify the location of a predetermined location on the stud (e.g., the edge of the stud, the center of the stud, or both) when the sensors (cooperating with one or more processors and audio and/or visual indicators) identify that the predetermined location on the stud has been reached. For example, the indicia on the housing, in one embodiment, is simply a marker hole in the housing. In another embodiment, the indicia may comprise a visual display on the housing, indicating a location corresponding to a feature (e.g., edge or center) of a stud.

In the embodiment where a hole is used as the indicia, the hole is substantially centered within the substantially circular configuration of the electrodes. In this embodiment, because the marker hole is equally spaced from all positions on the edge or perimeter of the electrodes, the marker hole will always be located at a predetermined location with respect to the stud, irrespective of the direction or angle the stud is reached from. This will be described in greater detail below. Just for example, in one embodiment, a substantially circular and/or interdigitating sensor configuration can have a diameter of about 2.0", or in one embodiment a diameter in the range of 1.5" to 2.5" and in yet another embodiment, a diameter in the range of 1.0" to 3.0". A diameter of 1.5" corresponds to the width of certain stud types (along its edge) that would normally engage with (or be immediately behind) the dry wall. Thus, in one example for a circular sensor with a diameter of 1.5", if the hole through the housing is centered between the sensors, the center of the hole will essentially be 0.75" from the perimeter of the sensor(s) in all directions. Thus, if a back surface of a housing of the sensing apparatus (also referred to herein as a stud finding device, or simply stud finder) is slid across the wall surface in any direction, then, when the perimeter of the substantially circular configuration of the sensors first reaches the edge of a stud underlying the wall surface, the center of the hole will be positioned 0.75" from the stud edge (or substantially centered with that particular stud type). It must be appreciated that that this will be true regardless of whether the stud finder's housing is moved perfectly horizontally along the wall surface (e.g., perpendicular to the stud), at a 45 degree angle or less with respect to the stud, or optionally at any angle of approach to the stud.

Figure 1B:
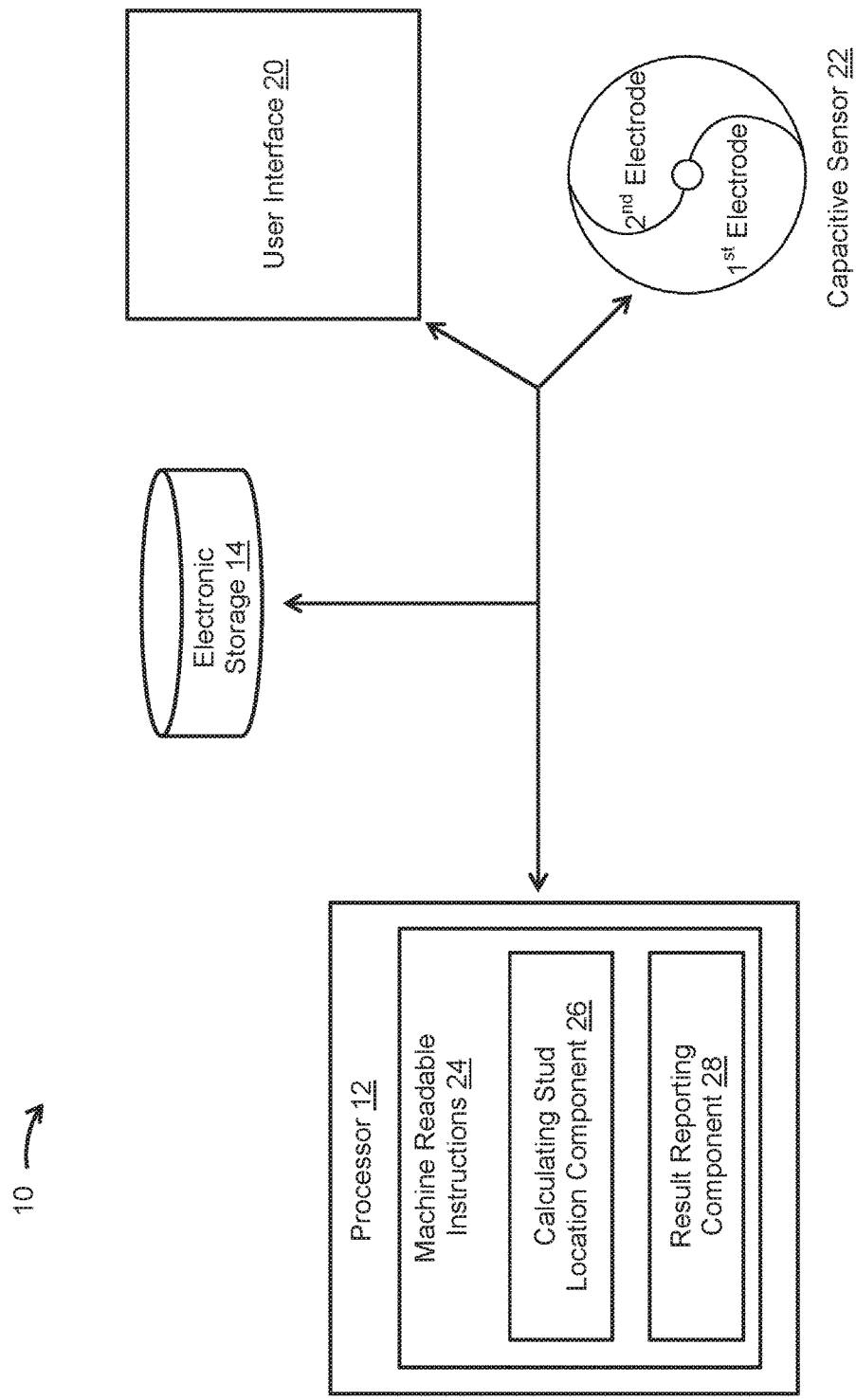
FIG. 1B is a schematic illustration of a stud sensing circuitry included in the stud sensing apparatus that enables locating a stud according to one or more embodiments of the present disclosure.

FIG. 1A depicts an exemplary front view of a stud sensing apparatus 100 (also referred to herein as a stud detecting apparatus) according to one embodiment of the present disclosure. The stud sensing apparatus 100 is configured to locate a stud using circuitry 10 illustrated in FIG. 1B. The stud sensing device 100 (referred to hereinafter as stud finder) is configured to facilitate a user to locate a stud without having to align the device 100 in a perfect vertical orientation, or moving the device 100 in a perfect linear and horizontal fashion. In some embodiments, and as shown in FIG. 1B, the stud finder includes one or more of, a processor 12, electronic storage 14, and a capacitive sensor 22 (also referred to herein as a stud sensor). By one embodiment, each of the processor 12, the capacitive sensor 22, and the electronic storage 14 may be coupled to a user interface 20. The user interface 20 provisions for instance, functions such as tuning the parameters of the capacitive sensors and the like. Details regarding this are described later with reference to FIG. 25. In some embodiments, processor 12, electronic storage 14, and the capacitive sensor 22 may reside in the same housing. In some embodiments, a microcontroller may be included in the same housing within which capacitive sensor 22 resides, and may be communicatively coupled with processor 12, electronic storage 14, and capacitive sensor 22. In some embodiments, capacitive sensor 22 may reside within a handheld housing.

The capacitive sensor(s) 22 may comprise two or more electrodes that may or may not be interdigitating. Moreover, the stud finder 100 may further comprise one or more processors. The one or more processors may be communicatively coupled with the capacitive sensor (22).

Processor 12 may be configured to provide information processing capabilities in stud finder 100. As such, processor 12 may comprise one or more of a digital processor, an analog processor, a digital circuit designed to process information, an analog circuit designed to process information, a state machine, and/or other mechanisms for electronically processing information. Although processor 12 is shown in FIG. 1B as a single entity, this is for illustrative purposes only. In some embodiments, processor 12 may comprise a plurality of processing units. These processing units may be physically located within the same device (e.g., a server or the housing within which capacitive sensor 22 resides), or processor 12 may represent processing functionality of a plurality of devices operating in coordination (e.g., a server, computing device and/or other devices.)

Furthermore, processor 12 can be configured via machine-readable instructions 24 to execute one or more computer program components. The one or more computer program components may comprise one or more of a calculating stud location component 26, a result reporting component 28, and/or other components. Processor 12 may be configured to execute components 26 and/or 28 by software; hardware; firmware; some combination of software, hardware, and/or firmware; and/or other mechanisms for configuring processing capabilities on processor 12.

It should be appreciated that although components 26 and 28 are illustrated in FIG. 1B as being co-located within a single processing unit, in embodiments in which processor 12 comprises multiple processing units, one or more of components 26 or 28 may be located remotely from the other component. The description of the functionality provided by the different components 26 and 28 described below is for illustrative purposes, and is not intended to be limiting, as any of components 26 and 28 may provide more or less functionality than is described. For example, one or more of components 26 and 28 may be eliminated, and some or all of its functionality may be provided by other components. As another example, processor 12 may be configured to execute one or more additional components that may perform some or all of the functionality attributed below to one of components 26 and/or 28.

In some embodiments, calculating stud location component 26 may be configured to calculate a stud location by measuring a change in capacitance from a fixed capacitance of a wall structure as the stud sensor is moved along a surface of the wall structure, as known in the art. Result reporting component 28 may be configured to report a result relating to a location of a stud.

In one embodiment, the stud sensor 22 uses capacitive sensing electronics to locate the center of studs and joists through a drywall or other common building materials and provides to a user an indication, either visually and/or audibly once a detection is made. The thickness of the building materials where stud is located may be 0.5", 0.75", 1" and up to 1.5" or more (or less than 0.5"), as known in the art. Use with any other suitable thicknesses is contemplated. By one embodiment, the stud detecting device of the present disclosure may also detect AC lines behind the surface of the drywall or other common building materials. Those AC lines carry the electrical power being delivered to homes and businesses. AC voltages may be in the range of 100-240V and AC frequencies may be in the range of 50-60 Hz. Use with lower and higher frequencies is contemplated.

Stud sensor 22 detects a capacitive change to a sensor when a stud is present behind the surface of a wall structure. In some embodiments, "charge transfer in self mode" technology is the capacitance measurement technology used to measure a change in capacitance based upon a fixed capacitance of the wall structure. There are several companies that produce "charger transfer" integrated circuit (IC) chips for user applications including Texas Instruments' CapTIvate technology.

"Self-mode" refers to the external capacitance change relative to earth ground. There are three different capacitors: a Vreg capacitor (not shown), a sampling capacitor (not shown), and an external unknown capacitor(s) (the first and second electrodes of the capacitive sensor 22, as shown in FIG. 1B) in hardware to implement the charge transfer technology. During the charge phase, the capacitance charge stored on the Vreg capacitor is used to charge the external unknown capacitance. Then a transfer phase begins, and the charge from the external capacitance is transferred to a sampling capacitor. In the meantime the Vreg capacitor is recharged by a DC linear voltage regulator. These charge and transfer phases are repeated until the sampling capacitor is charged to a preset amount.

In some embodiments according to the present technology, the external capacitance is the electrode's capacitance change when there is stud or similar structure present. The hardware to implement this capacitance measurement is part of the peripheral of the microcontroller. The microcontroller's charge transfer engine settings are configured in software to provide high sensitivity of the system.

Figure 15:
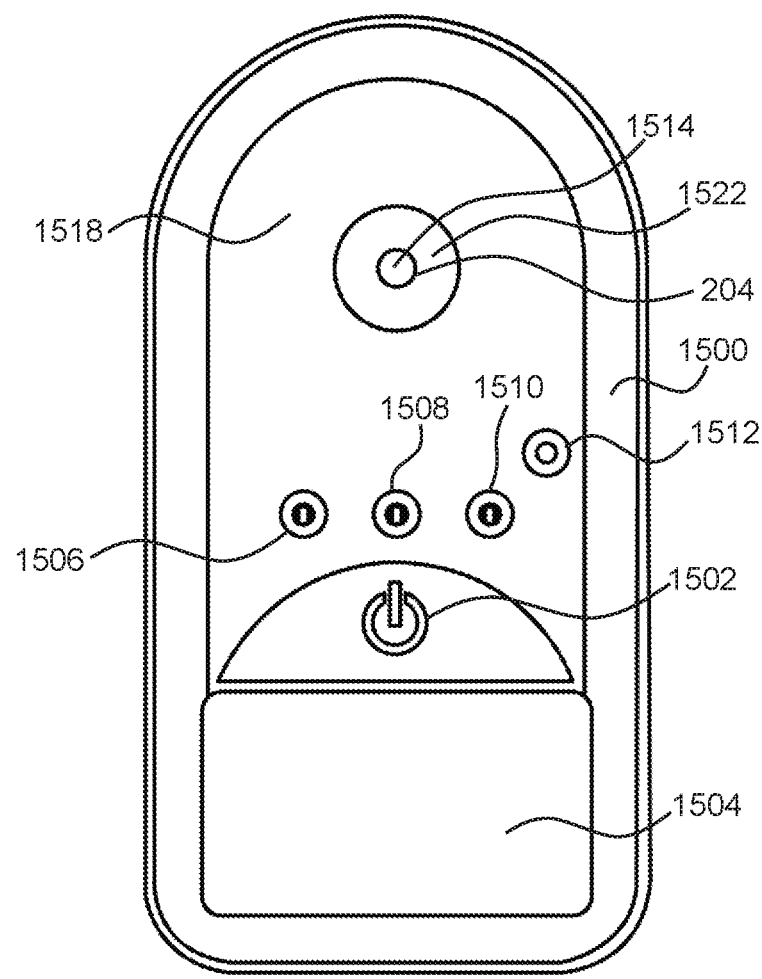
FIGS. 15-24 illustrate various views of a housing of a stud sensor according to one or more embodiments.

In one embodiment, the housing 101 (FIG. 1A) is provided with an indicia thereon to advise the user where, in relation to the housing the identified attribute of the located stud (edge or center) is located. For example, the indicia can be a pointer on the housing, an LED display on the housing, or simply a hole through the housing (as in the illustrated embodiment). Further details regarding the housing and the associated components of the stud finder 100 are described later at least, with reference to FIG. 15.

Figure 2:
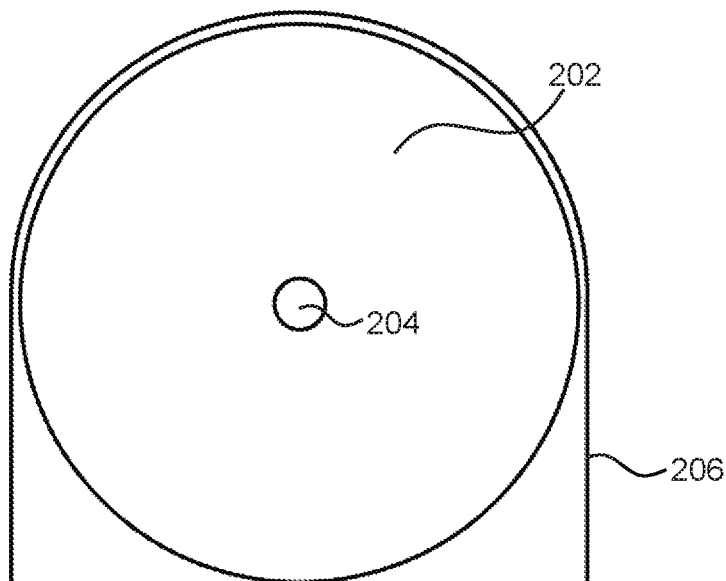
FIG. 2 illustrates a shield electrode according to one or more embodiments.

By way of a non-limiting example, FIG. 2 illustrates an optional first shield electrode 202 (solid shield plane) according to one or more embodiments. In one embodiment, the shield electrode 202 is substantially circular (like the capacitive sensor electrodes), and in one embodiment the shield electrode 202 has an outer diameter that is larger than the outer diameter of the substantially circular sensor electrodes that for the capacitive sensor 22. In another embodiment, the shield electrode 202 has an outer configuration that is not substantially circular. A hole 204 (or center marking channel) is provided through the center of first shield electrode 202. In some embodiments, the hole (or center marking channel) through the center of first shield electrode 202 may be aligned, or at least partially aligned, with a back hole 1514 that is disposed on a back side of the housing (e.g., through the back half of a clam shell housing) of the stud finder (see FIG. 15). In some embodiments the hole 204 may also extend through the front of the housing (e.g., through a front half of a claim shell housing). In one embodiment, the hole at the front of the housing may be larger (or smaller) than the hole at the back of the housing. In one embodiment, the hole 204 extends through the housing and through the shield electrode (as well as the substantially circular and/or interdigitating electrodes forming the capacitive sensor as will be described). As such, the hole is substantially centered with respect to the periphery of these electrodes. The hole is configured to be aligned with an edge of a stud, or in some embodiments with the center of a stud, when an audio and/or visual indicator reports a result related to a location of a stud. For example, the audio indicator can take the form of a speaker, vibrator, or other noise maker that emits a sound when the edge (and/or center) of a stud is reached or located. In addition, or alternatively, a visual indicator such as an LED, LCD, or other visual indicator can provide a visual indication, when the edge (and/or center) of a stud is reach or located. A pencil or pen may be inserted through hole 204 to mark the wall surface at a location of the wall behind which a stud has been detected. In another embodiment (not illustrated), rather than a hole (and instead of the user using a pen or pencil to mark the wall surface), the central region of the housing (where the hole 204 is located) can instead be provided with a spring biased button. The button has a finger engaging surface at the front side of the housing, and an extendable pin or pointed projection that is normally withdrawn inside the housing and can be forced rearwardly beyond the back surface of the housing, against the spring bias of the button when the button is depressed by a user, to engage the wall surface to create a small hole or mark on the wall surface. The small hole or mark created by the pin or pointed projection will correspond to the center of the stud, when a stud has been detected.

By one aspect of the present disclosure, the first shield electrode 202 is disposed on a back side (placed in apposition or substantially in apposition with a wall structure) of a printed circuit board (PCB) 206. Moreover, the first shield electrode 202 is driven at a same potential as the two interdigitating electrodes 302 and 304 of FIG. 3. The utility of the shield electrode as well as its relative positioning with respect to the PCB and the interdigitating electrodes is described next with reference to FIG. 3.

In the embodiment where a hole 204 is used as the indicia, the hole is substantially centered within the substantially circular configuration of the electrodes. This can be appreciated from the configurations shown in FIGS. 6-9. In these embodiments, because the marker hole 204 is equally spaced from all positions on the edge or perimeter of the electrodes, the marker hole will always be located at a predetermined location with respect to the stud, irrespective of the direction or angle the stud is reached from. For instance, the stud finder need not be held perfectly in a vertical fashion in order to detect the stud. Even if the stud finder is disposed at an angle with respect to the wall, the stud finder of the present disclosure enables accurate detection of the stud due to the configuration of the capacitive sensors described herein. Just for example, in one embodiment, a substantially circular sensor configuration can have a diameter of 1.5" (which corresponds to the width of certain stud types along its edge that would normally engage (or be immediately behind) the dry wall. If the hole 204 though the housing and centered between the sensors is centered, the center of the hole will essentially be approximately 0.75" from the perimeter of the sensors in all directions. Thus, if the stud sensor housing back surface is slid across the wall surface in any direction, when the perimeter of the substantially circular configuration of the sensors first reaches the edge of a stud underlying the wall surface, the center of the hole will be positioned 0.75" from the stud edge (or substantially centered with that particular stud type). This will be true whether the stud finder housing is moved perfectly horizontally along the wall surface (e.g., perpendicular to the stud), at a 45 degree angle or less with respect to the stud, or optionally any angle of approach to the stud.

Figure 3:
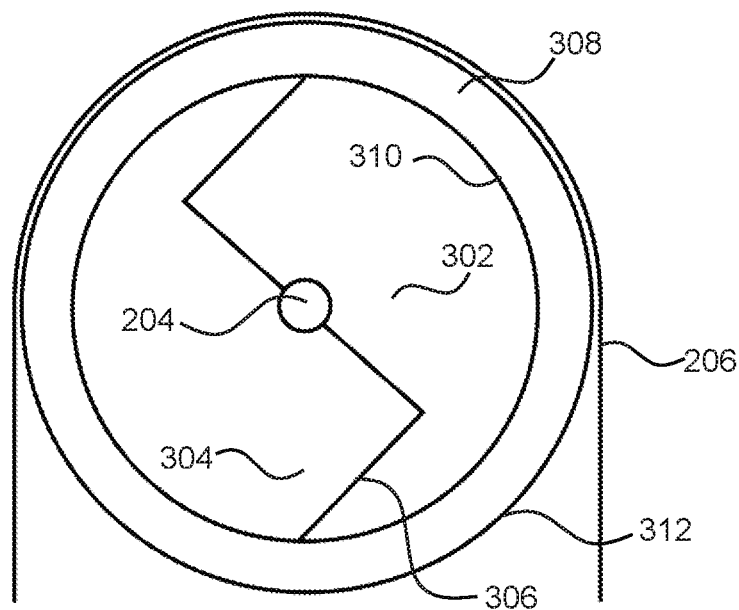
FIG. 3 illustrates two interdigitating electrodes according to one or more embodiments.

FIG. 3 illustrates two interdigitating electrodes according to one or more embodiments. The term "interdigitating" as used herein is defined to mean folded or locked together. This may mean, for example, that one electrode may not be moved relative to another electrode on at least one axis. The two interdigitating electrodes include first electrode 302 and second electrode 304. In some embodiments, the electrodes may not be interdigitating. In one embodiment, there is a gap 306 formed between first electrode 302 and second electrode 304, and an outer perimeter 312. In some embodiments, gap 306 may be approximately 0.2 mm, however, any other suitable values are contemplated. For instance, the gap 306 may be in the range from 0.05 mm to 0.3 mm, and in another embodiment, in the range 0.15 mm to 0.25 mm Note that the gap 306 provides insulation between the first electrode 302 and the second electrode 306.

By one embodiment of the present disclosure, it is envisioned that a second shield electrode 308, that is substantially ring-shaped, may be included in the stud sensor. Accordingly, the first electrode 302, second electrode 304, first shield electrode 202, and second shied electrode 308 form a capacitive sensor. The sensor design choice provides sufficient sensitivity and minimizes noise from parasitic capacitance. By one embodiment, the interdigitating electrodes are disposed on a top layer of PCB 206, and surrounded at its periphery by second shield electrode 308. The first shield electrode 202 can be disposed by one embodiment, across the bottom layer of the PCB. The first shield electrode 202 and second shield electrode 308 are electrically coupled and/or communicatively coupled with respect to each other and with respect to first electrode 302 and second electrode 304. There is a gap 310 between the electrodes (first electrode 302 and second electrode 304) and second shield electrode 308. In some embodiments, gap 310 may be approximately 0.8 mm, however, any other suitable values are contemplated. For instance, the gap 310 may be in the range 0.5 mm to 0.8 mm, and in one embodiment, in the range of 0.6 mm to 0.7 mm. The combination of charge transfer in self mode technology with an interdigitating electrode sensor enables accurate detection of stud centers on thicker walls over other stud finders on the market. An accelerometer, humidity detector, and temperature detector may provide increased reliability.

The shield electrodes disclosed herein are optional, and can be omitted from the embodiments described. When they are provided, they provide various functionality to the stud finder. For example, in some embodiments they can reduce noise because they are the ground plane of the PCB. Secondly, the shield electrodes are driven at the same potential as first electrode 302 and second electrode 304.

This driven shield minimizes the parasitic capacitance and increases the sensor's sensitivity.

Figure 4:
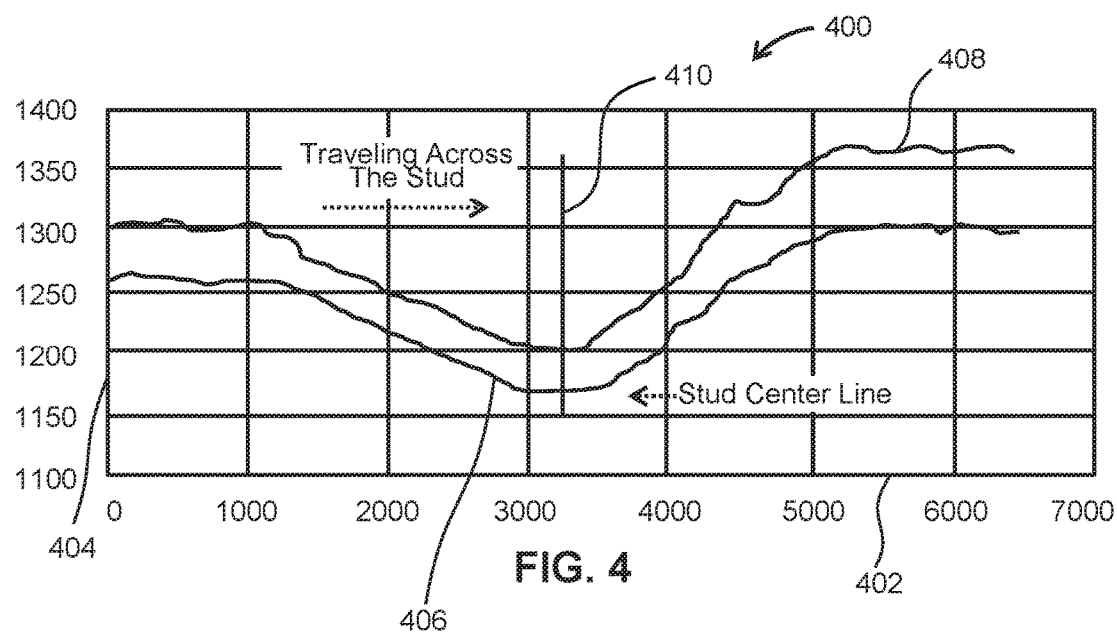
FIG. 4 is an exemplary graph depicting signals corresponding to two electrodes according to one or more embodiments.

In some embodiments, the combination of first electrode 302 and second electrode 304 generate a total of two signals that indicate a change in capacitance when there is stud behind the surface of the wall structure and the stud is in proximity with the capacitive sensor. The signal value will drop gradually when the electrodes 302 and 304 (i.e., together the capacitive sensor) passes over the stud and gradually increase after the capacitive sensor passes the stud as shown in FIG. 4. The software and/or firmware in a microcontroller can be configured to continuously monitor the signal values. The changes in value is recognized by software and/or firmware and used to determine the presence and/or location of a stud.

By way of a non-limiting example, FIG. 4 illustrates two electrodes' signal graph 400 according to one or more embodiments. The horizontal axis 402 represents the number of samples of capacitance taken as capacitive sensor 22 travels across a surface of a wall structure (from left to right in this case). The vertical axis 404 does not have units, but represents a relative change in capacitance as capacitive sensor 22 travel across the surface. Waveform 406 represents a signal reading from first electrode 302. Waveform 408 represents a signal reading from second electrode 304. The signals are at their lowest points at stud center line 410. When the waveforms reach this low point, capacitive sensor 22 is centered over the stud. For instance, referring to FIG. 1B, when sweeping capacitive sensor 22 from left to right, for example, the electrode to the sensor's right (i.e., the electrode labeled as the $2^{nd}$ electrode) would be activated when encountering a stud. Subsequently, the electrode to the sensor's left (i.e., the electrode labeled as the $1^{st}$ electrode) would be activated as the electrode to the sensor's right is being deactivated.

The number and area of the electrodes are selected to provide sufficient signal strength to detect a stud through the maximum specified thickness of wall based on the capacitance equation:

$$C=E \times A/d \qquad \text{Equation 1}$$

where E is the dielectric constant, A is the area of contact of sensor 22 (i.e., the circular area of the capacitive sensor 22) with a wall structure, and d is the distance between the capacitive sensor and the stud (or the wall thickness in some embodiments).

In some embodiments, the sensor is designed in substantially circular shape for symmetry. One aspect of the substantially circular shape, as explained above, is that the signals (see FIG. 4) are tolerant of the angle of the movement of capacitive sensor 22. One embodiment, the capacitive sensor 22 will work best when the user approaches a stud at an angle of less than 45° (movement by the user). This is because at greater angles, the two electrodes may approach the stud at the same time (e.g., if the stud sensor approached the stud at 90°, with the top part of the housing moving into/toward the stud). Of course, this angle can be engineered and designed as desired.

FIG. 5 is a wall depth table according to one or more embodiments. In capacitance equation 1 above, the area of the combination of two electrodes is in direct relationship to capacitance. This table defines, in some embodiments, the minimum round area of two electrodes with respect to wall depth that will generate good and reliable detection capacitance change results. The numbers in this wall depth table are merely exemplary in nature and not intended to be limiting. Other values are envisioned.

FIG. 6 illustrates two interdigitating electrodes forming a substantially circular configuration according to one or more embodiments. A first electrode 602 and a second electrode 604 separated by an interface 606. A hole 204 (or 1514, see FIG. 15) is provided through the electrodes (or at the interface between the electrodes) as illustrated and discussed herein. A yin-yang or s-shaped pattern may be formed in the embodiment of FIG. 6. First electrode 602 and second electrode 604 may meet at a variety of different curves and/or line segment(s). The substantially circular configuration formed by the two electrodes of FIGS. 6-9 may have a diameter ranging between approximately 1" to 3". However, other values are contemplated. Moreover, in one embodiment, the diameter of the shield electrode 202 is greater than the diameter of the circular configuration formed by the first electrode 602 and the second electrode 604. For instance, the diameter of the shield in one embodiment is in the range 1.5" to 3.5". In another embodiment, the shield electrode has a diameter than is smaller than the first electrode FIG. 7 illustrates two electrodes forming a substantially circular configuration according to one or more embodiments. A first electrode 702, and a second electrode 704 meet at a gap 706 and a hole 204 as discussed herein. First electrode 702 and second electrode 704 are each in the shape of a semi-circle, or a substantially semi-circular shape. Interface 706 is in the form of a line segment with hole 204 there through. The configuration of the electrode illustrated in FIG. 7 is not interdigitating.

FIG. 8 illustrates two interdigitating electrodes forming a substantially circular configuration according to one or more embodiments. A first electrode 802 and a second electrode 804 meet at interface or gap 806 and comprises a hole 204 there through as discussed herein. A saw-tooth or zig-zag pattern is formed by the interface for the embodiment of FIG. 8. Interface 806 has three line segments with the central line segments having hole 204 there through.

FIG. 9 illustrates two interdigitating electrodes forming a substantially circular configuration according to one or more embodiments. A first electrode 902 and a second electrode 904 meet at interface or gap 906 and comprises hole 204 as discussed herein. As can be seen in FIG. 9, the interface between first electrode 902 and a second electrode 904 comprises a plurality of curved lines. All other suitable patterns are contemplated but are not shown herein for the sake of brevity.

Interdigitating electrodes provide higher sensitivity than non-interdigitating electrodes. If there are N number of electrodes, the ratio of each electrode's area to the whole area of the substantially circular capacitive place is 1:N in some embodiments. In one embodiment, the shape of a given electrode is the mirror image of the other electrode within the circular area; those electrodes are interlocking (interdigitating) in some embodiments. However, it must be appreciated that the N electrodes that are interdigitated form a substantially circular configuration.

Figures 10, 11:
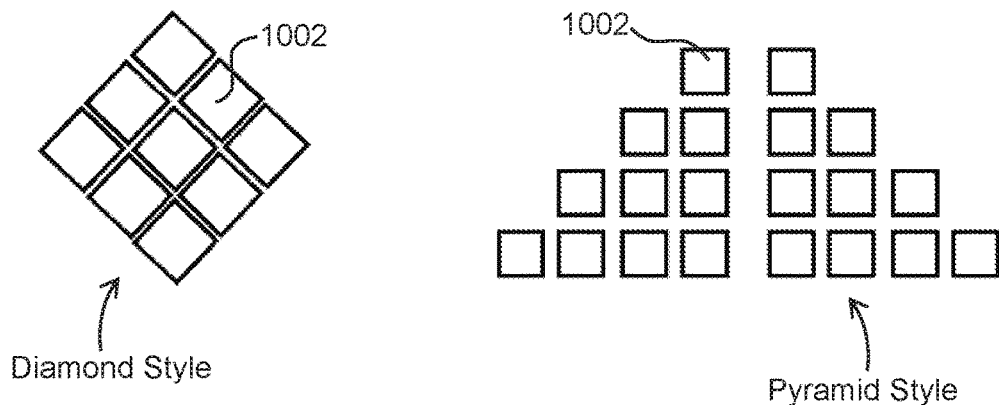
FIG. 10 illustrates arrays of substantially square electrodes forming various structures according to one or more embodiments.
FIG. 11 is a wall depth table according to one or more embodiments.

FIG. 10 illustrates arrays of substantially square two-dimensional electrodes forming various structures according to one or more embodiments. The diamond pattern comprises multiple square electrodes arranged in an N×N array and formed in substantially diamond shape. The pyramid pattern comprises multiple square electrodes arranged in N×M array and formed in a substantially pyramid shape. The configuration of electrodes enables capacitive sensor 22 to be omnidirectional. Stud sensor 22 may be moved at any angle and still detect a predetermined or desired location of stud (e.g., the edge or center) irrespective of the angle at which the wall engaged back surface of the housing of capacitive sensor 22 is oriented with respect to the wall.

Additionally, based on the location of the electrodes and changes in electric potential of the electrodes, stud sensing device 100 may indicate the orientation of a stud. These attributes may also apply to other embodiments, such as the embodiments of FIGS. 6-9. For example, as described in the U.S. Provisional Application No. 62/354,176, (and with reference therein to FIGS. 5 and 6A), the electrodes overlapping the stud area constantly changes due to the shape of the electrodes as the stud finder is moved across the wall. Accordingly, as the capacitance of certain electrodes (within the pyramid or diamond style configuration of FIG. 10) changes, the stud finder may be configured to estimate the orientation of the stud.

By one embodiment, the substantially circular configuration of electrodes enables capacitive sensor 22 to be omnidirectional. In contrast, as a rectangular electrode crosses over a stud, the overlap area with respect to the electrode and the stud will not increase at a predictable rate if the rectangular electrode is not aligned vertically. For example, a corner of the electrode may first overlap a stud if the electrode is not aligned vertically with respect to a wall structure. Providing a substantially circular configuration overcomes this problem and allows for the sensor to not be aligned vertically and to be moved in a non-linear fashion.

FIG. 11 is a wall depth table according to one or more embodiments. This table defines, in some embodiments, the minimum square electrode area of a square electrode with respect to wall depth that will generate clean and reliable detection capacitance change results. The numbers in this wall depth table are merely exemplary in nature and not intended to be limiting. Other values are envisioned.

Figure 12:
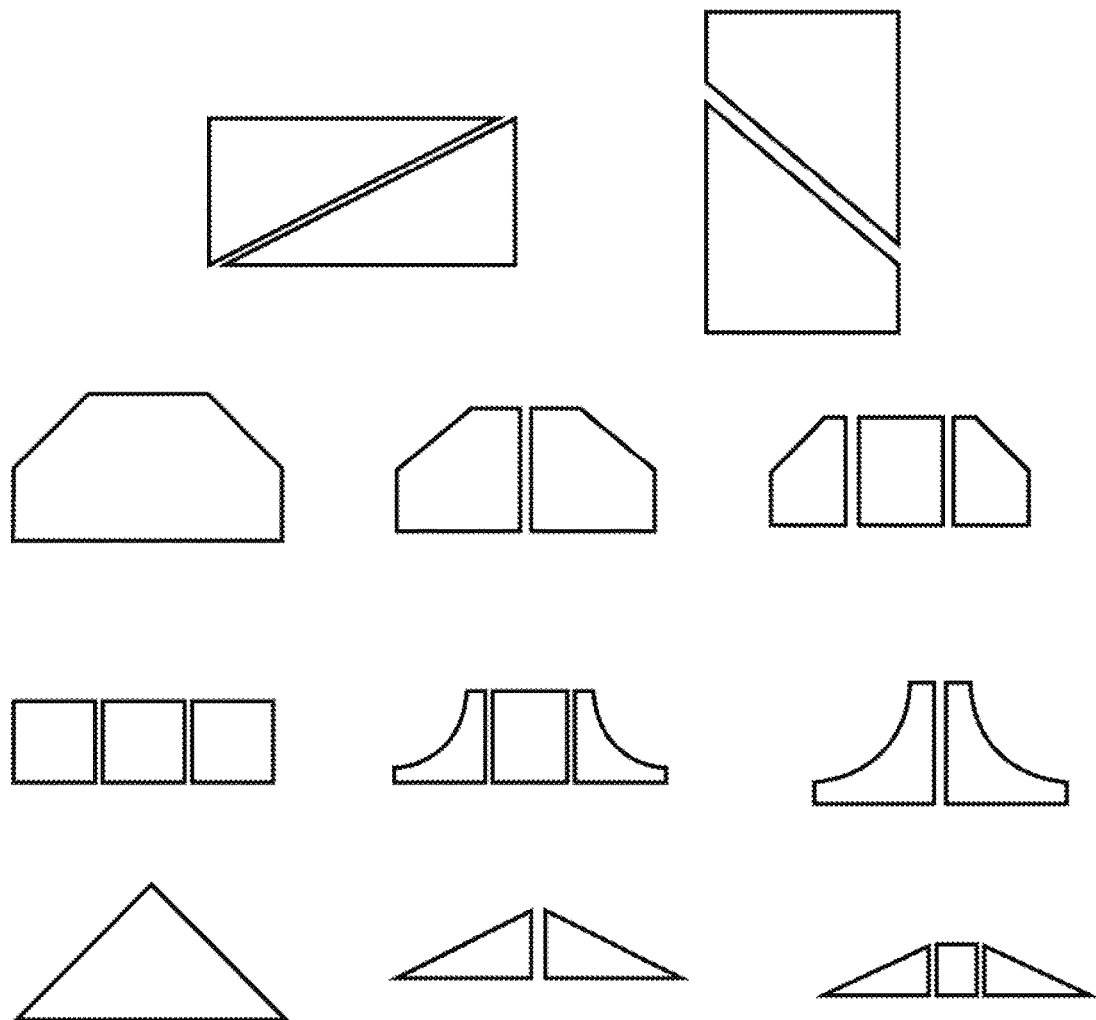
FIG. 12 illustrates various examples of electrodes in substantially triangular patterns and other patterns according to one or more embodiments.

FIG. 12 illustrates various examples of electrodes in substantially triangular patterns and other patterns according to one or more embodiments. These patterns were discussed in U.S. Provisional Application No. 62/354,176, filed on Jun. 24, 2016 and titled "STUD FINDER," the content of which is incorporated herein in its entirety by reference. The patterns comprise one or multiple modified forms of substantially triangular or substantially rectangular electrodes. During operation, the part of the electrode overlapping the stud area is changing due to the shape of electrode. The changing area generates a direct proportional capacitance change. Moreover, the relationship between the shape and overlapping area is explained in FIGS. 6A and 6B of the '176 provisional patent application.

Figure 13:
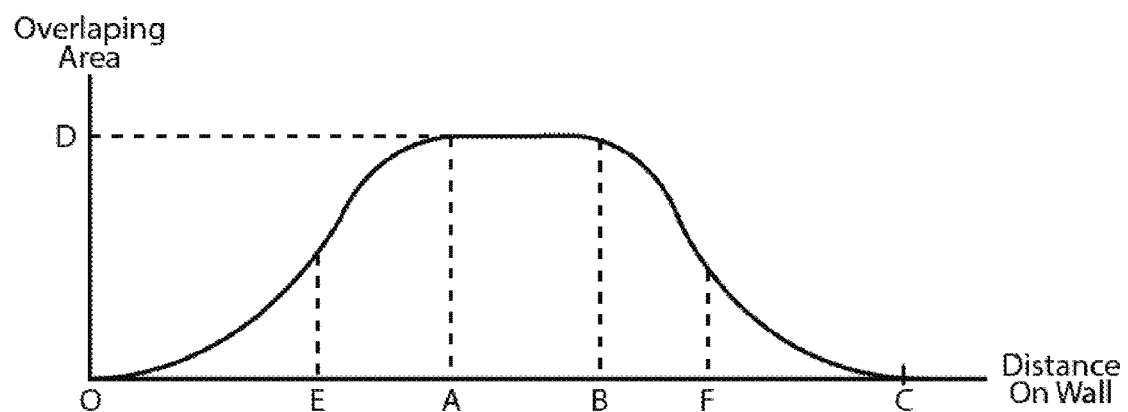
FIG. 13 is a graph illustrating a progression of overlapping area of a substantially triangular capacitive plate according to one or more embodiments.

FIG. 13 is a graph illustrating a progression of overlapping area of a substantially triangular capacitive plate according to one or more embodiments. FIG. 13 corresponds to FIG. 6A of the '176 provisional patent application and was described therein.

Figure 14:
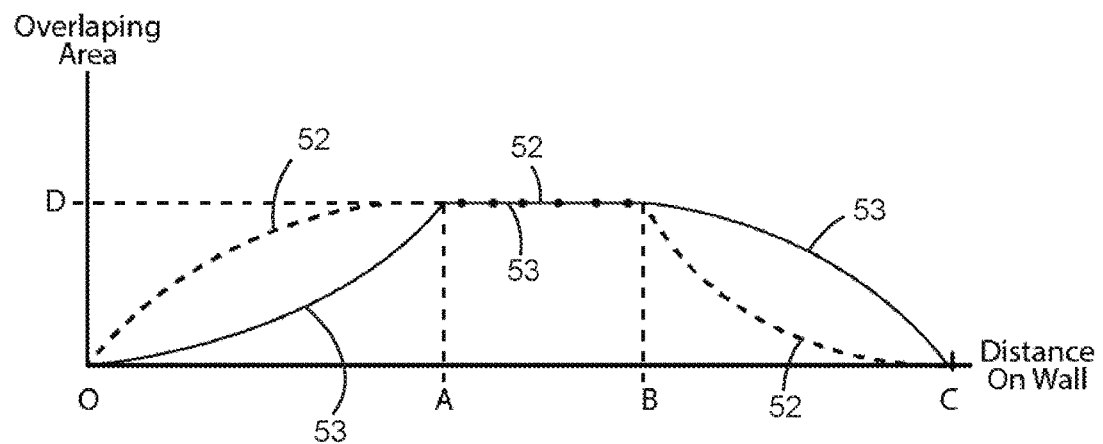
FIG. 14 is a graph illustrating a progression of overlapping area of non-rectangular capacitive plates according to one or more embodiments.

FIG. 14 is a graph illustrating a progression of overlapping area of non-rectangular capacitive plates according to one or more embodiments. FIG. 14 corresponds to FIG. 6B of the '176 provisional patent application and was described therein.

FIGS. 15-24 illustrate various views of designs of a housing of capacitive sensor 22 according to one or more embodiments. In some of the figures, back hole 1514 is depicted as smaller than hole 204. However, in some embodiments back hole 1514 is larger than hole 204 and may be located at the front of housing 1500 with hole 204 being smaller and located at the back of housing 1500. FIGS. 15-19 differ aesthetically with respect to FIGS. 20-24, as can be seen in the figures. In some embodiments, the sensor and electronic control circuits are laid out in one PCB and the top side of PCB is enclosed in a plastic housing 1500. The housing is designed to be user-friendly and ergonomic. The back of the PCB is covered in an overlay material made of adhesive-backed film with a thickness of approximately 0.005". However, other values are envisioned. The overlay material may or may not include labeling. This material is better than the felt pads used on the most current stud finders in the market because it provides very smooth movement and reduces the assembly parts. Furthermore, the use of the overlay material also eliminates an air gap that is created by using multiple smaller pads, thus increasing dielectric coupling. Because the product slides smoothly on the wall, it can start and stop quickly so the user gets an accurate location of a stud center.

In some embodiments, housing 1500 includes power button 1502, battery compartment 1504, LEDs 1506, 1508, and 1510, AC detector LED 1512, hole 204, and back hole 1514. In some embodiments, hole 204 may have a diameter greater than that of back hole 1514; however, this need not be the case. In some embodiments, hole 204 may have a diameter less than that of back hole 1514. In some embodiments, hole 204 may have a diameter equal to that of back hole 1514. In some embodiments, hole 204 may be the hole through the center of the capacitive plate formed from first electrode 302 and second electrode 304 and may be located at the back of housing 1500. The back of housing 1500 is the face of the housing that is put in apposition with a surface of a wall structure. Hole 204 may go through first electrode 302, second electrode 304, and form an opening in the back of housing 1500 that may lead to a surface of a wall structure. In some embodiments, hole 1514 may be the hole through the center of the capacitive plate formed from first electrode 302 and second electrode 304. In some embodiments, hole 204 may be the back hole and what was referred to as back hole 1514 may be the hole in the front of housing 1500. The front of housing 1500 is the part of housing 1500 that is opposite to the back of housing 1500. The front of housing 1500 is not put in apposition with a surface of a wall structure. The user may view the front of housing 1500 while sweeping the back of housing 1500 across a surface of a wall structure. The front of housing 1500 may include elements such as LEDs and a power button in some embodiments. Battery compartment 1504 may be configured horizontally (as in FIG. 15) or vertically (as in FIG. 20). A hole (1514) formed through the housing 1500 may be centered or substantially centered with respect to the hole (204) formed between the capacitive plates (i.e., the first electrode 302 and second electrode 304).

Another feature of housing 1500 is the power button's location and design, which assists the user in holding the housing 1500 evenly on a wall structure, thereby generating a clean signal. Yet another feature standing out from the current stud finder products is the thin profile of the body which can be easily put into user's pocket.

As mentioned previously, an opening (hole 204) in the center of sensor 22, and correspondingly the opening 1514 on the housing of the stud finder are intended for the user to draw a mark on the wall through the opening when the stud is detected. In doing so, encourages the user to mark the center of the detecting electrodes instead of the traditional linear offset marking channel, eliminating some potential for error.

In some embodiments, when the housing 1500 is swept across the surface of a wall structure, LED 1506 lights up (i.e., activated), when a stud is proximate to capacitive sensor 22 and to the left of the center of the sensor (the electrodes) of capacitive sensor 22. When sweeping the housing 1500 across the surface of a wall structure, LED 1510 lights up when a stud is located approximately at the center of the sensor of capacitive sensor 22 and to the right of the center of the sensor of capacitive sensor 22. At that point, the user can use a pencil or pen to mark the wall surface through the hole 204, which should be aligned with the center of the stud at that point. When sweeping housing 1500 across the surface of a wall structure, LED 1508 lights up when a stud is approximately at the center of the sensor of capacitive sensor 22. Again, at that point, the user can use a pencil or pen to mark the wall surface through the hole 204, which should be aligned with the center of the stud at that point. Other forms of reporting the location of a stud (or more specifically, a position on the stud such as the edge or center) are contemplated, such as audio signals, digital readouts, vibration, etc. AC detector LED 1512 lights up when an AC line is located. Audio or graphical display may also be used to indicate the detection of an AC line. Other forms of reporting the location of an AC line are contemplated.

Figure 16:
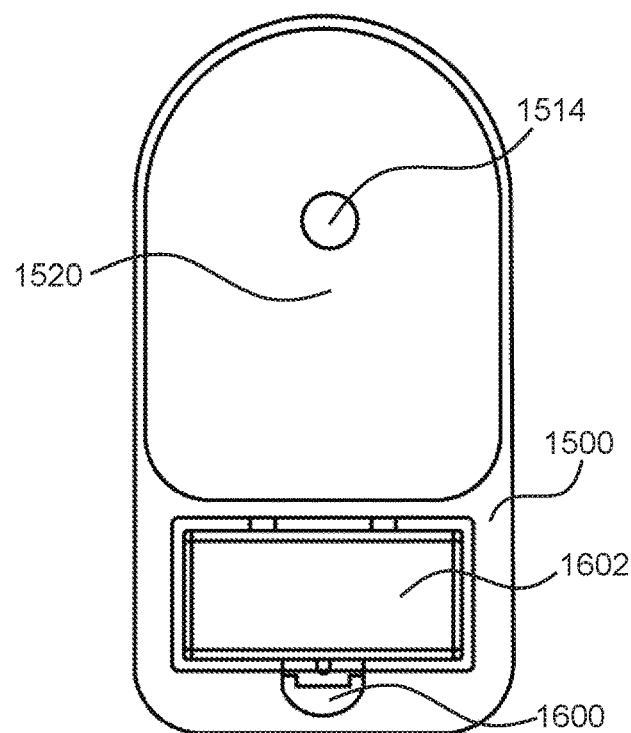
Figure 17:
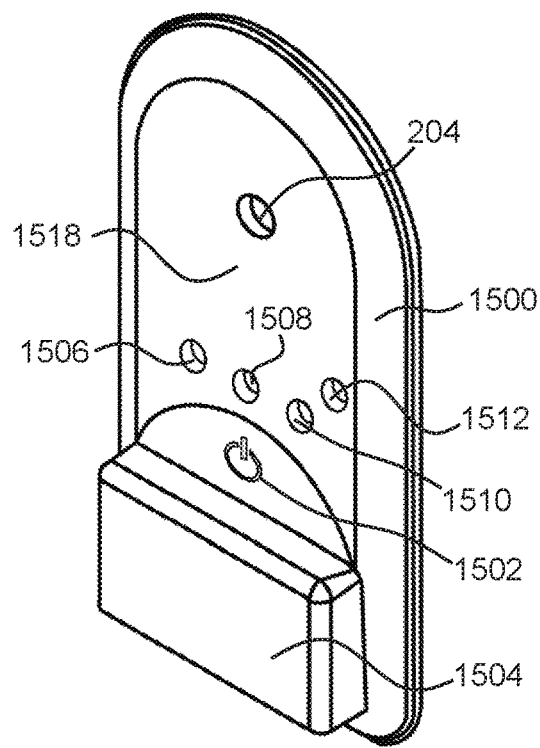
Figure 18:
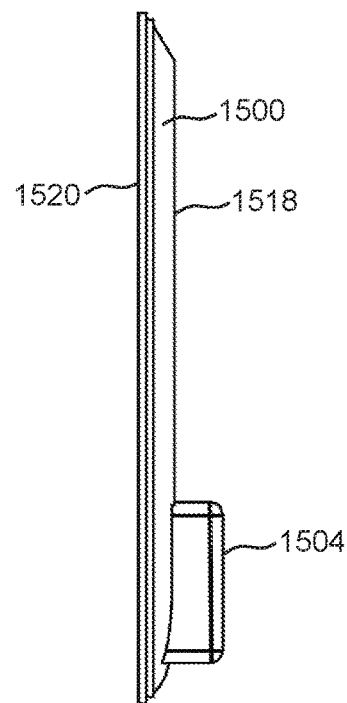
Figure 19:
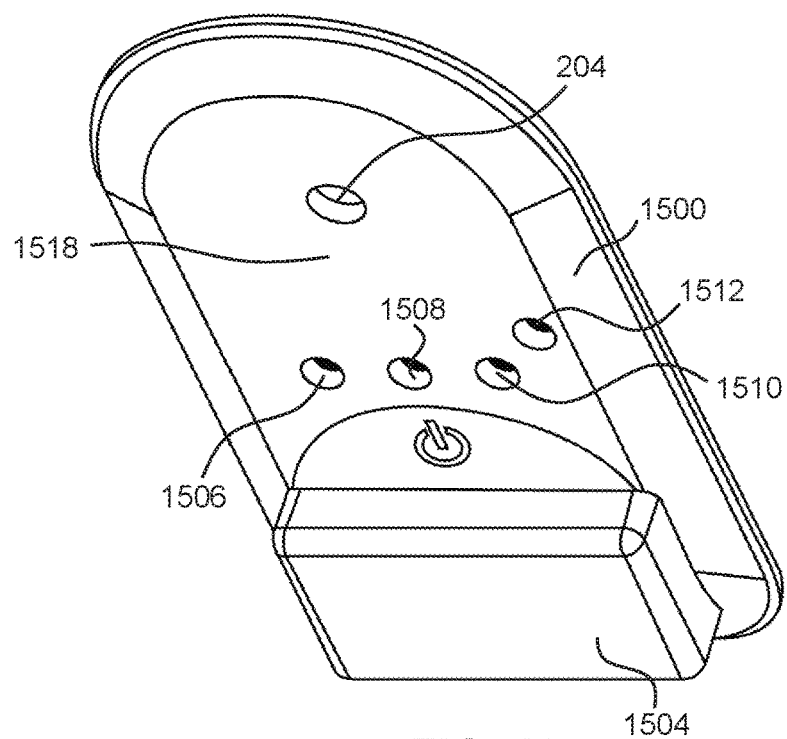

FIG. 16 illustrates a back view of housing 1500, whereas FIG. 17 depicts an isometric view of the stud finder 100. Moreover, FIGS. 18 and 19 depict a side view, and a trimetric view of the stud finder, respectively. Referring to FIG. 16, tab 1600 may be actuated to open battery cover 1602 of battery compartment 1504 (as shown in FIG. 17). In some embodiments, the back hole may be hole 204. In some embodiments, the back hole may be back hole 1514 and may be smaller than hole 204. This holds true for all the figures in some embodiments.

Figure 20:
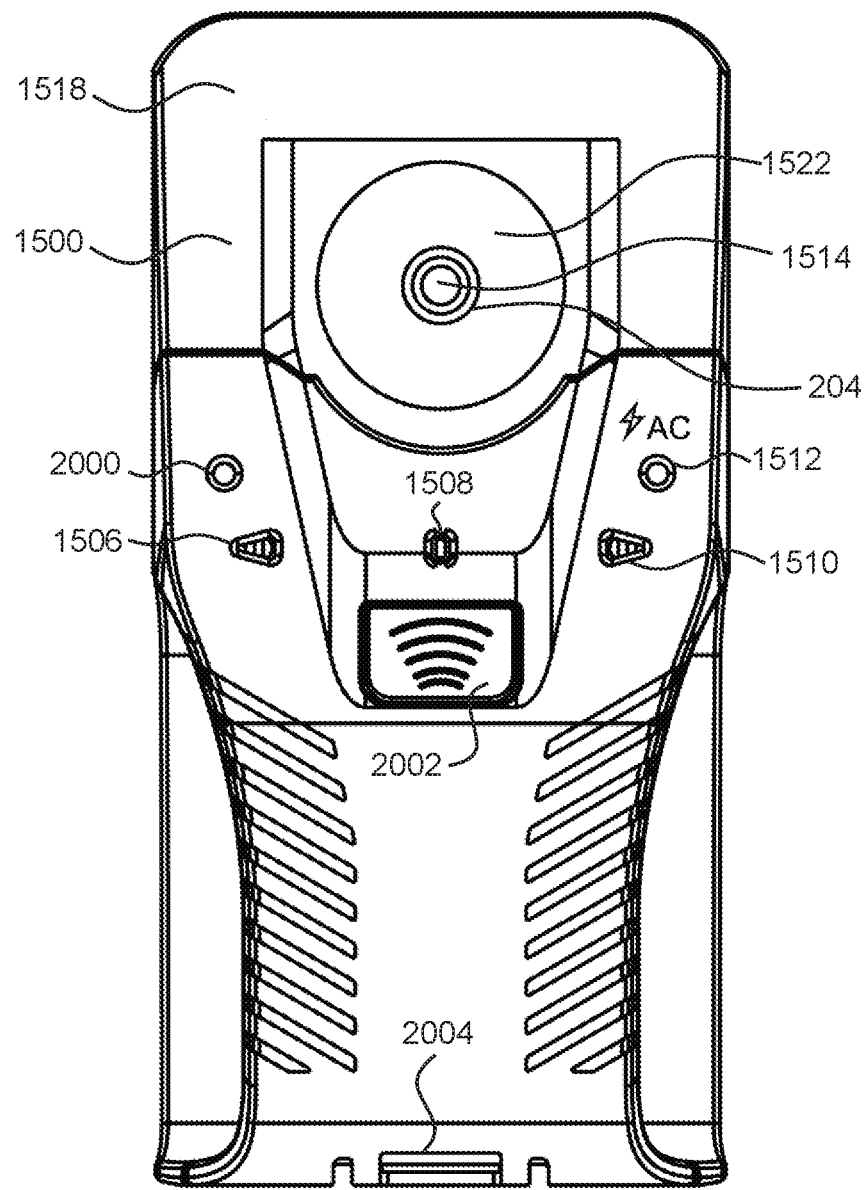

FIG. 20 illustrates a front view of another design of housing 1500. In some embodiments, housing 1500 additionally includes a power on LED 2000, a power button 2002, and a cover 2004 to a battery compartment that is configured vertically instead of horizontally.

Figure 21:
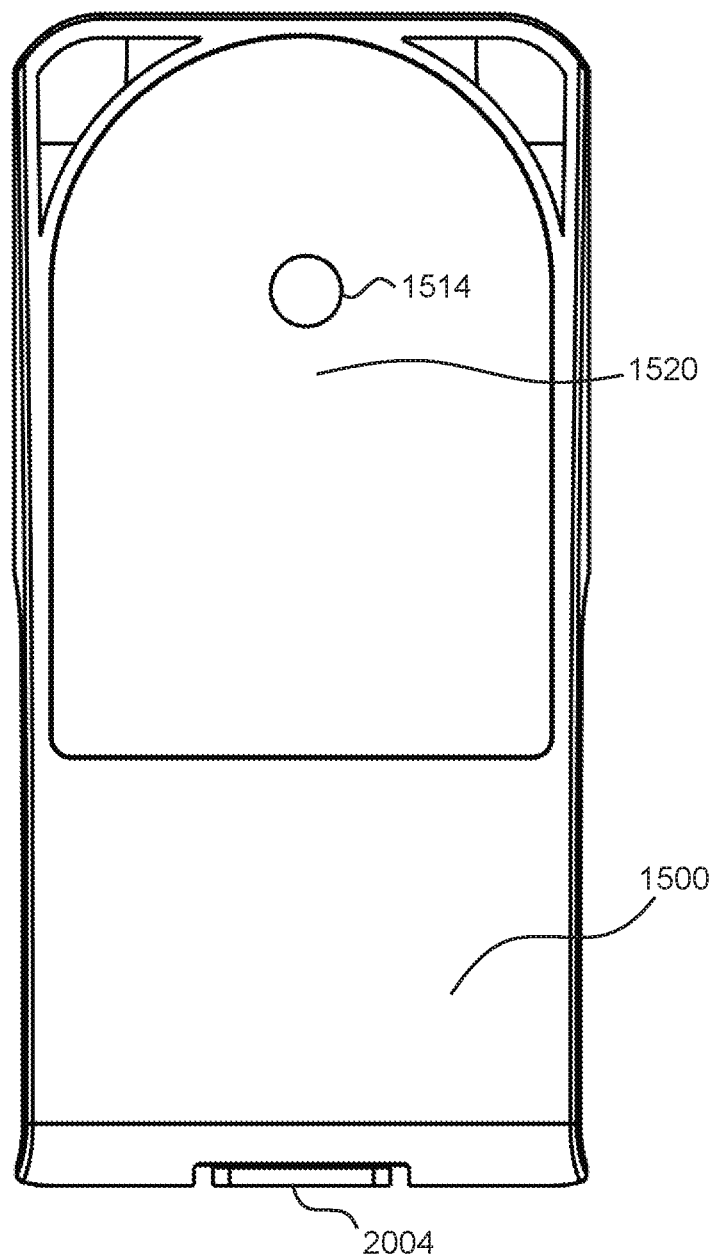
Figure 22:
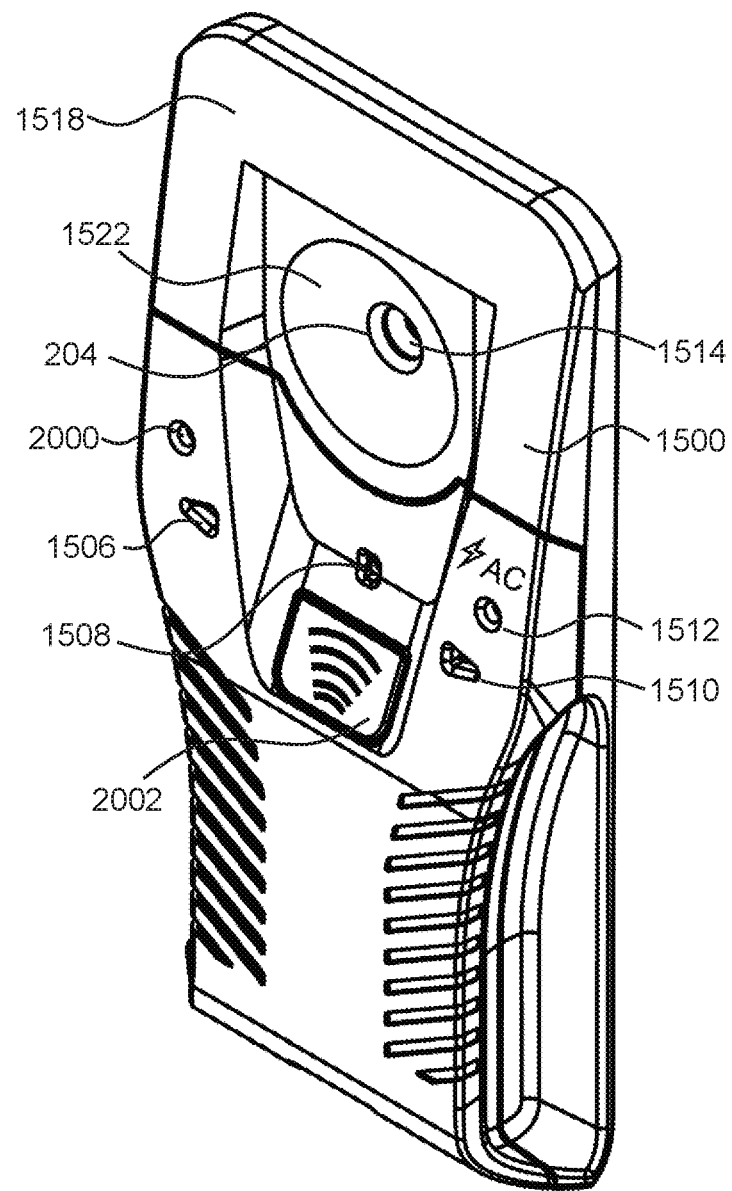
Figure 23:
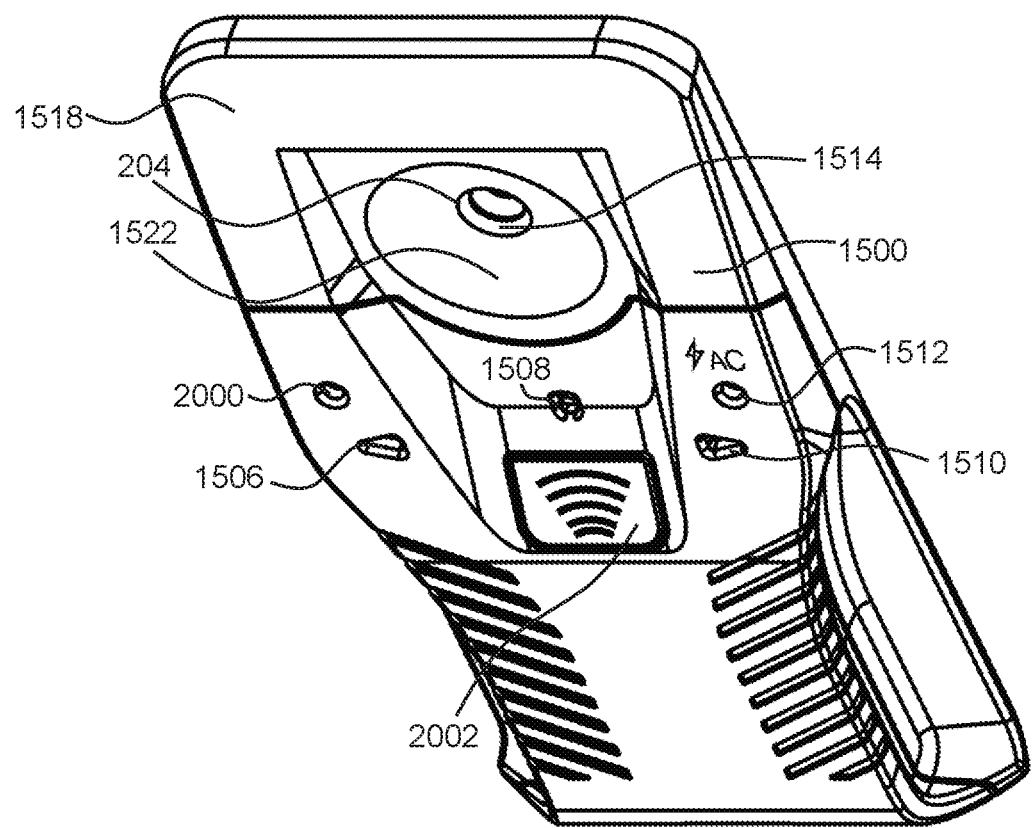
Figure 24:
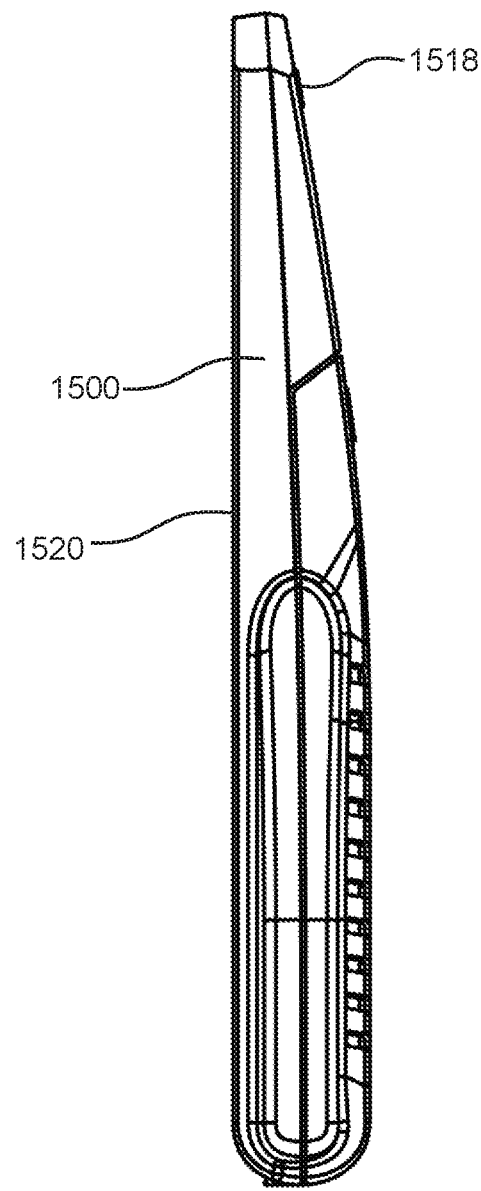

FIG. 21 illustrates a back view of the design of housing 1500 of FIG. 20. Hole 1514 and cover 2004 to the battery compartment are shown. FIGS. 22 and 23 depict isometric and trimetric views of the stud finder of FIG. 20, whereas FIG. 24 illustrates a side view of the design of housing 1500 of FIG. 20.

Figure 25:
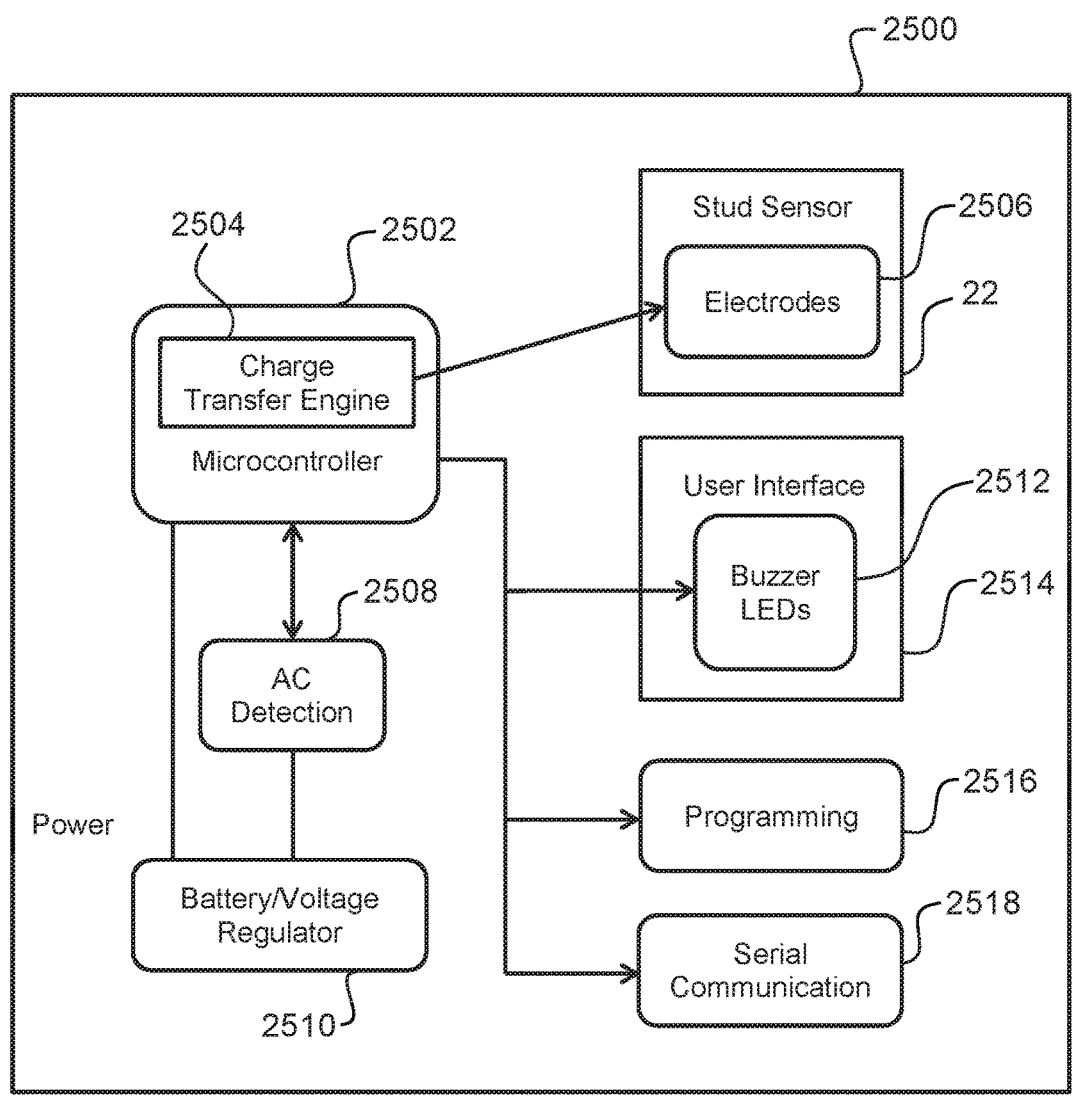
FIG. 25 illustrates an electronic hardware block diagram according to one or more embodiments.
Figure 26:
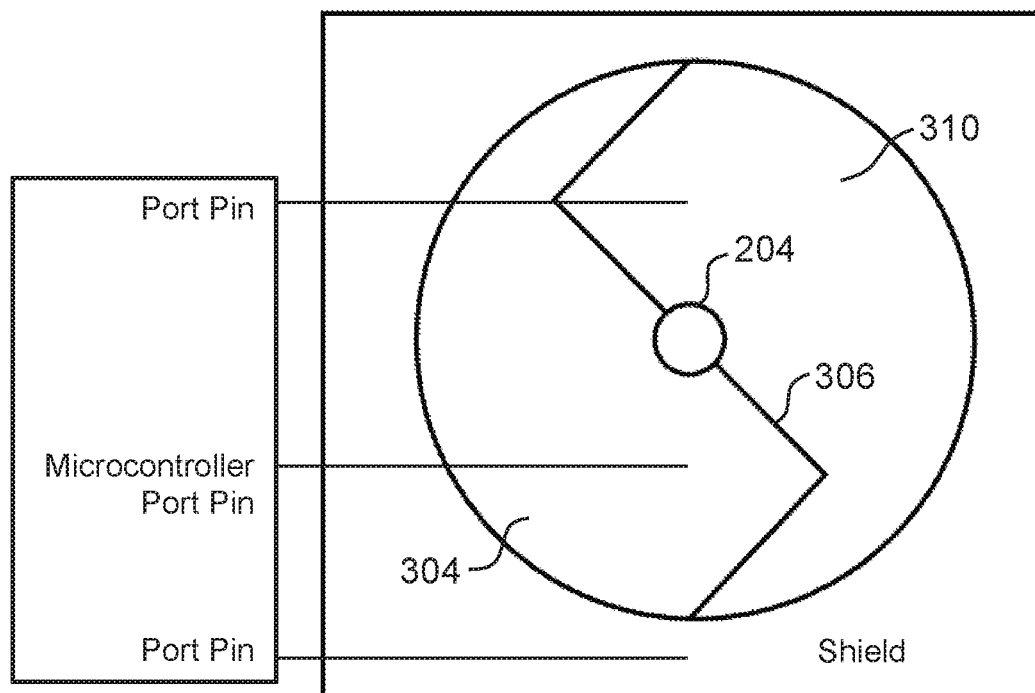
FIG. 26 illustrates an electrode connection diagram according to one or more embodiments.
Figure 27:
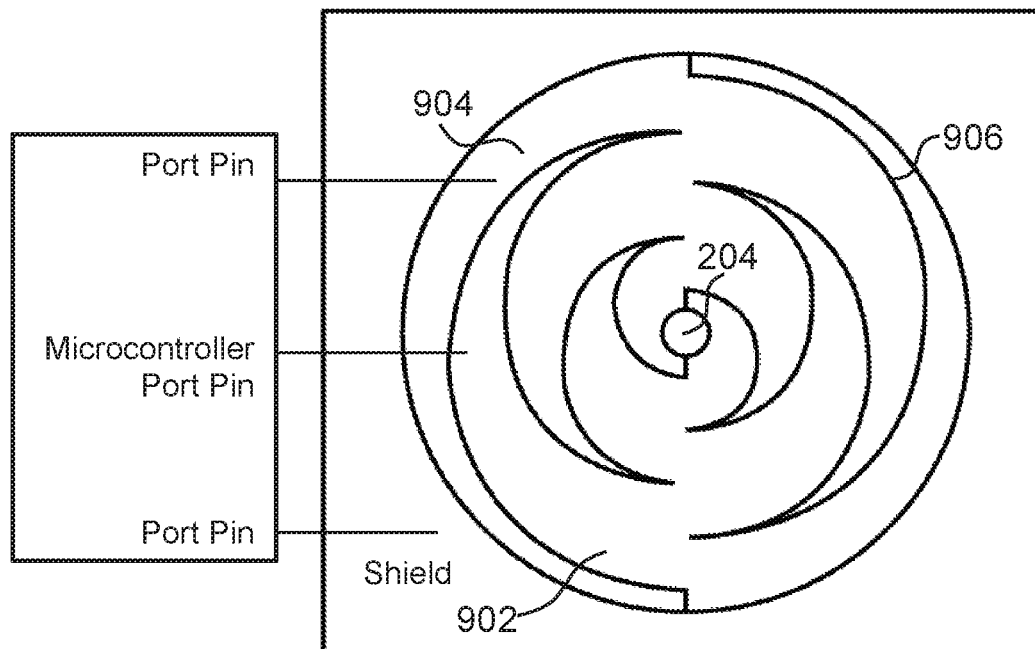
FIG. 27 illustrates an electrode connection diagram according to one or more embodiments.

FIG. 25 illustrates an electronic hardware block diagram 2500 according to one or more embodiments. In some embodiments, electronic hardware block diagram 2500 may comprise a microcontroller 2502, a charge transfer engine 2504, electrodes 2506 (the sensor of capacitive sensor 22), an AC detection module 2508, a battery/voltage regulator 2510, a buzzer/LEDs (that may be part of user interface 2514), a programming connector 2516, a serial communication block 2518, and/or other elements. Microcontroller's 2502 integrated charge transfer engine 2504 may use charge transfer technology to measure the capacitance change in electrodes 2506 (the sensor of capacitive sensor 22) because each electrode is a self-capacitive sensor in some embodiments. In some embodiments, each electrode including the shield node is mapped to the charge transfer engine's 2504 port pin as shown in FIGS. 26 and 27. The control of the charge and transfer phases and the conversion rate are configured in charge transfer engine 2504 and controlled by charge transfer engine 2504. Microcontroller 2502 scans the electrodes in parallel. This capability reduces the scan time and power consumption. In some embodiments, charge transfer engine 2504 may be integrated in microcontroller 2502. In some embodiments, charge transfer engine 2504 may be outside of microcontroller 2502.

In some embodiments, as indicated, a buzzer and visual indicators such as LEDs (or other indicators) may be part of user interface 2514. A buzzer may sound and a colored visual indicator such as red light on the housing may light up when the center of a stud is detected. Other colored visual indicators such as, for example, a yellow light may light up when approaching or leaving the stud area. When an AC line is detected, a buzzer may sound and a colored visual indicator such as red light on the product may light up to indicate there is AC line within a specified distance from the device. Programming connector 2516 connected to microcontroller 2502 may enable a program on the PCB to be updated using a computer. Serial communication block 2518 may enable microcontroller 2502 to send and receive the data through a serial port on microcontroller 2502.

By one embodiment, because of the fast electrode scanning time and low power consumption, capacitive sensor 22 is able to be powered by low power sources such as, for example, 2 AAA batteries. The small size of the batteries allows housing 1500 to be small and portable. In some embodiments, the hardware design may use surface-mount components. This reduces assembly time and cost. Because, in some embodiments, there are no through-hole components on the back side of the PCB, the overlay material may be directly applied over the back of the PCB without the need for another smooth plate. This further reduces assembly time and cost, and also allows housing 1500 to be small and portable.

Firmware of the stud finder may run on microcontroller 2502. The firmware may comprise, in some embodiments, three main software segments: charge transfer engine configuration code, stud sensor application code, and data communication code.

The charge transfer engine configuration code sets the capacitance mode to SELF mode; assigns all the sensor elements to the appropriate port pins on microcontroller 2504; and optimizes sensor 22 tuning parameters such as conversion gain, conversion count, and scan time to create high sensitivity for stud detection. It scans the sensors in parallel, which reduces operating time and saves battery power. It also automatically calibrates the sensor data so the system does not require a user to wait for a few seconds for calibration after powering up.

In some embodiments, the stud sensor application code is designed with an algorithm to detect a stud behind the surface of walls of 0.5" and 0.75" thickness. However, other values (e.g., 1" and 1.5") are also contemplated. During various running cycles, firmware reads in the raw capacitance data from capacitive sensor 22, smooths out the noise in the data, and checks the current data against the previous data to look for the data trend direction. In FIG. 4, it is shown that the stud center is located when the waveforms reach their lowest points. Data moves in a downward trend when approaching a stud and an upward trend when leaving a stud. As soon as the data changes from a downward trend to an upward trend, the firmware will alert the user with a colored visual indicator (or other indicator) such as red light and buzzer sound to indicate a stud is detected. The firmware sets a threshold of the capacitance data value change for different wall thicknesses. If the capacitance data value change does not reach the threshold, it will not be recognized by the software as a valid stud in order to prevent misdetection. This threshold value is also used to predict a wall's thickness.

AC detection circuits send a signal to microcontroller 2502 when an AC line is detected within a given distance range. The firmware (or software) will alert the user with a colored visual indicator (or other indicator) such as red light and buzzer sound to indicate the AC line has been detected.

Figure 28:
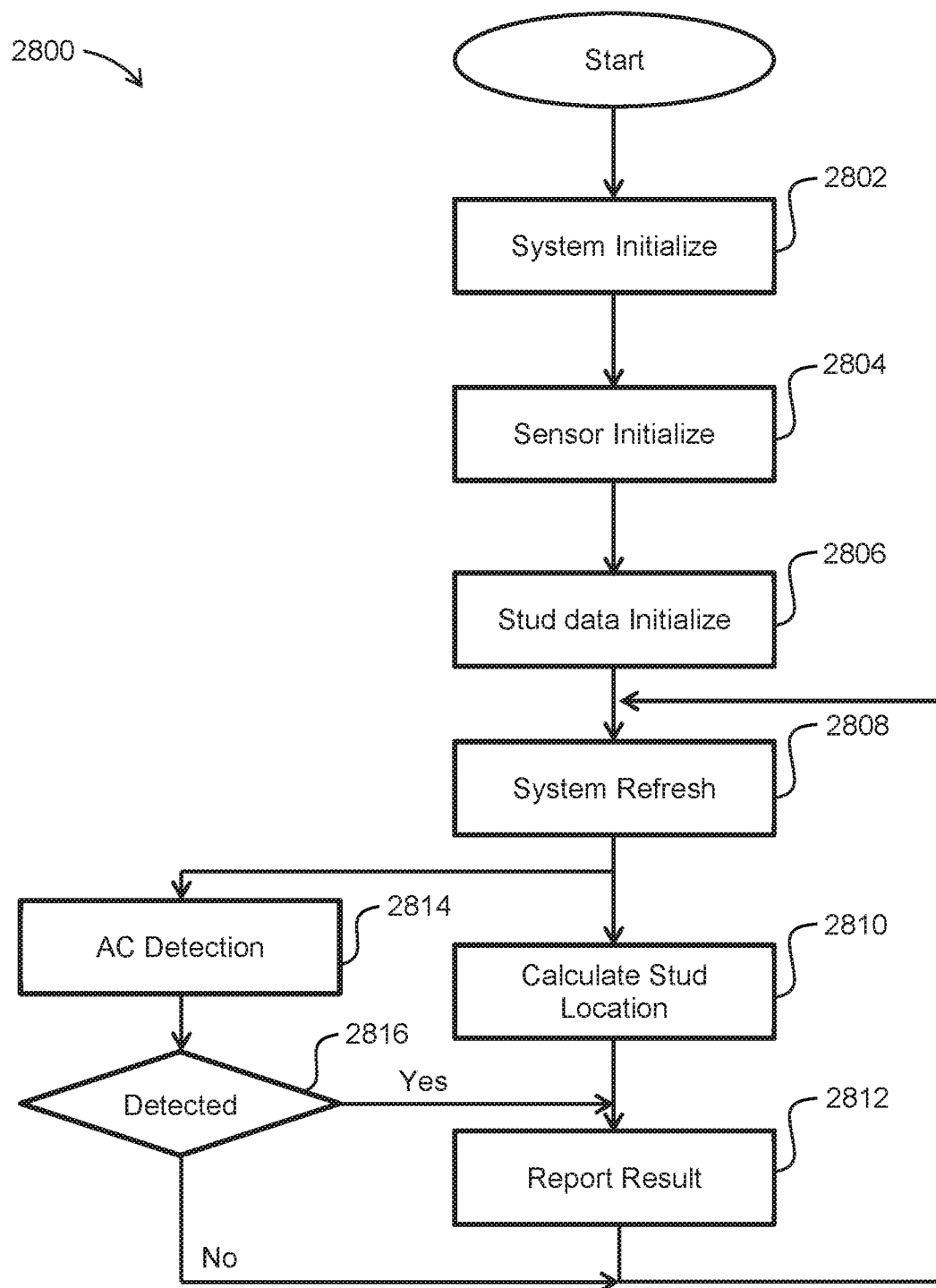
FIG. 28 illustrates a firmware or software flowchart according to one or more embodiments.

FIG. 28 illustrates a firmware or software flowchart 2800 according to one or more embodiments. At an operation 2802, the stud finder can be initialized. This may include adjusting various setting, and performing a setup operation including configuring communication ports and microcontroller 2502.

At an operation 2804, the sensor (two electrodes that may be interdigitating, and the shield electrode) of capacitive sensor 22 are initialized. This may include setting up a configuration for the electrodes and changing various settings, parameters, etc. For instance, by one embodiment, the previously described functions performed by the charge transfer engine are performed in this step.

At an operation 2806, stud data may be initialized by setting at least one capacitance variable to a specified value.

At an operation 2808, a system refresh is performed so the stud data is read from the two or more electrodes, the data being related to a capacitance behind a surface. This capacitance variable will change as capacitive sensor 22 approaches a stud and a measured capacitance changes. The capacitance variable represents the measured capacitance at a location behind a surface of a wall structure. More specifically, one or more processors modify the capacitance variable as a measured capacitance of the wall structure at a position of the sensor with respect to the wall structure changes, the capacitance variable being directly proportional to the measured capacitance of the wall structure at the position of the sensor.

At an operation 2810, a stud location is calculated by determining when the waveforms of FIG. 4 reach their lowest point. That is, when the capacitance and capacitance variable(s) reach their lowest value(s). In some embodiments, detecting the location of a stud may include detecting an edge of a stud, a center of a stud, or both. In some embodiments, a picture of an entire stud may be shown. In other words, an array of LEDs may be implemented and only the LEDs that are determined to be above the stud may be illuminated. In this way, a user may see where the middle and/or ends of the stud are located. Alternatively, a single LED may be utilized to indicate when the center of the stud is detected.

At an operation 2812, when a stud has been located a result is reported to the user. This may be done if a variety of ways. For example, LEDs, a graphical display, audio, etc. may be used to indicate proximity of a stud or an exact or substantially exact location of a stud. The process then proceeds to operation 2808. The refresh may be automatic in some embodiments. The refresh may be initiated manually in some embodiments.

At an operation 2812, AC line detection is performed as is known in the art.

At an operation 2816, AC detector LED 1512 lights up if an AC line is detected. Audio or a graphical display may also be used to indicate the detection of an AC line. The process then proceeds to operation 2812. If no AC line is detected, then the process proceeds to operation 2808. The refresh may be automatic in some embodiments. The refresh may be initiated manually in some embodiments.

Figure 29:
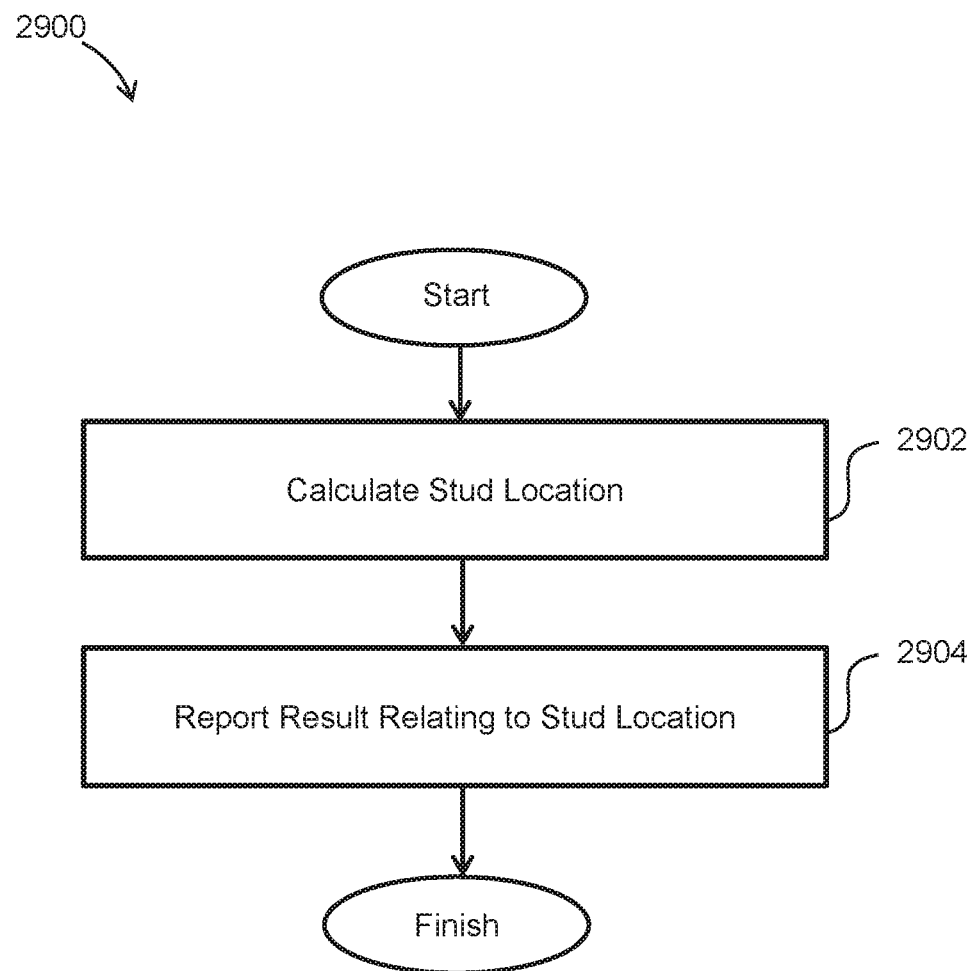
FIG. 29 illustrates a method for locating a stud with a stud sensor according to one or more embodiments.

FIG. 29 illustrates a method 2900 for locating a stud with capacitive sensor 22 configured to locate a stud according to one or more embodiments. Stud sensor 22 comprises housing 1500 and a sensor carried by housing 1500. The sensor comprises two or more electrodes. Stud sensor 22 further comprises one or more processors communicatively and/or electrically coupled with the two or more electrodes. In some embodiments, the two or more electrodes may be interdigitating. The one or more processors are configured by machine-readable instructions to execute computer program components. The computer program components comprise calculating stud location component 26, result reporting component 28, and/or other components.

The operations of method 2900 presented below are intended to be illustrative. In some embodiments, method 2900 may be accomplished with one or more additional operations not described, and/or without one or more of the operations discussed. Additionally, the order in which the operations of method 2900 are illustrated in FIG. 2900 and described below is not intended to be limiting.

In some embodiments, method 2900 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 2900 in response to instructions stored electronically on an electronic storage medium. The one or more processing devices may include one or more devices configured through hardware, firmware, and/ or software to be specifically designed for execution of one or more of the operations of method 2900.

At an operation 2902, the location of a stud is calculated. In some embodiments, operation 2902 is performed by a processor component the same as or similar to calculating stud location component 26 (shown in FIG. 1B and described herein).

At an operation 2904, results related to a stud location are reported. In some embodiments, operation 2904 is performed by a processor component the same as or similar to result reporting component 28 (shown in FIG. 1B and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A stud sensor configured to locate a stud, the stud sensor comprising:
   a housing;
   a sensor carried by the housing, the sensor comprising two or more electrodes, wherein the two or more electrodes are positioned next to each other to form a substantially circular configuration;

a shield electrode carried by the housing and disposed behind the sensor;

a hole through the housing centered between the sensor; and one or more processors carried by the housing, the one or more processors communicatively coupled with the sensor, the one or more processors configured by machine-readable instructions to:

calculate a stud location by measuring a change in capacitance from a fixed capacitance of a wall structure as the stud sensor is moved along a surface of the wall structure; and generate one or more signals to report a result relating to a location of a stud, wherein the hole is aligned with an edge of the stud upon the result being reported.

2. The stud sensor of claim 1, wherein the one or more processors are further configured by machine-readable instructions to modify a capacitance variable as a measured capacitance of the wall structure at a position of the sensor with respect to the wall structure changes, the capacitance variable being directly proportional to the measured capacitance of the wall structure at the position of the sensor.

3. The stud sensor of claim 1, wherein the two or more electrodes are arranged in an interdigitating configuration.

4. The stud sensor of claim 3, wherein the two or more interdigitating electrodes meet at a curve.

5. The stud sensor of claim 1, wherein the substantially circular configuration formed by the two or more sensors comprises a circle.

6. The stud sensor of claim 1, wherein the substantially circular configuration formed by the two or more sensors comprises an oval.

7. The stud sensor of claim 1, wherein the substantially circular configuration formed by the sensor comprises the two or more electrodes having a multi-sided shape that has at least eight sides.

8. The stud sensor of claim 1, further comprising an audio and/or visual indicator in communication with the one or more processors to receive the signal reporting the result relating to the location of a stud.

9. A stud sensor configured to locate a stud, the stud sensor comprising:

a housing;

a sensor carried by the housing, the sensor comprising two or more interdigitating electrodes;

a shield electrode carried by the housing and disposed behind the sensor; and one or more processors carried by the housing, the one or more processors communicatively coupled with the sensor, the one or more processors configured by machine-readable instructions to:

calculate a stud location by measuring a change in capacitance from a fixed capacitance of a wall structure as the stud sensor is moved along a surface of the wall structure, wherein the change in capacitance is calculated in a self-mode operation of the sensor, modify a capacitance variable as a measured capacitance of the wall structure at a position of the sensor with respect to the wall structure changes, the capacitance variable being a function of the measured capacitance of the wall structure at the position of the sensor, and generate one or more signals to report a result relating to a location of a stud.

10. The stud sensor of claim 9, wherein the two interdigitating electrodes meet at a curve.

11. The stud sensor of claim 9, wherein the two interdigitating electrodes form a substantially circular configuration.

12. The stud sensor of claim 11, wherein the substantially circular configuration comprises a circle.

13. The stud sensor of claim 11, wherein the substantially circular configuration comprises an oval.

14. The stud sensor of claim 9, wherein a hole through the housing and between the electrodes is substantially centered with respect to the interdigitating electrodes.

15. The stud sensor of claim 9, wherein the shield electrode is communicatively coupled with the one or more processors.

16. The stud sensor of claim 9, further comprising an audio and/or visual indicator in communication with the one or more processors to receive the signal reporting the result relating to the location of a stud.

17. The stud sensor of claim 16, further comprising a hole through the housing and between the electrodes, the hole being substantially centered with respect to the electrodes, wherein the hole is configured to be aligned with a center of the stud when the audio and/or visual indicator reports the result.

18. A method for locating a stud with a stud sensor configured to locate a stud, the stud sensor comprising a housing and a sensor carried by the housing, the sensor comprising two or more electrodes configured to form a substantially circular configuration, audio and/or visual indicators carried by the housing, a shield electrode carried by the housing and disposed behind the sensor, and one or more processors communicatively coupled with the two or more electrodes and the audio and/or visual indicators, the one or more processors configured to generate output signal to the audio and/or visual indicators when a result relating to a location of a stud is determined, and a hole through the housing centered between the sensors, the method comprising:

calculating a stud location by measuring a change in capacitance from a fixed capacitance of a wall structure as a back surface of the stud sensor housing is moved along a surface of the wall structure;

reporting a result relating to a location of a stud based on the change in capacitance;

indicating the result relating to the location of the stud via the audio and/or visual indicators; and wherein the hole is aligned with the location of the stud when the audio and/or visual indicators provide the indication, and irrespective of the angle at which the wall engaged back surface of the housing is oriented with respect to the wall.

19. The method of claim 18, wherein the hole is aligned with an edge of a stud when the audio and/or visual indicators provide the indication.

20. The method of claim 18, wherein the two or more electrodes are disposed in an interdigitating configuration.

* * * * *

UNITED STATES PATENT AND TRADEMARK OFFICE
CERTIFICATE OF CORRECTION

PATENT NO. : 10,571,423 B2
APPLICATION NO. : 15/632175
DATED : February 25, 2020
INVENTOR(S) : Bruce Eidinger et al.

Page 1 of 1

It is certified that error appears in the above-identified patent and that said Letters Patent is hereby corrected as shown below:

On the Title Page

Item (56) References Cited
Please add the following U.S. Patent document:
--7,786,981 B2 08/2010 Proctor--

Signed and Sealed this
Twenty-ninth Day of December, 2020

Andrei Iancu
*Director of the United States Patent and Trademark Office*